(12) United States Patent
Hastings et al.

(10) Patent No.: US 10,467,927 B2
(45) Date of Patent: Nov. 5, 2019

(54) PARAMETRICALLY ADJUSTABLE AIRWAY TRAINING MANNEQUIN WITH INSTRUMENTED PARAMETER ASSESSMENT

(71) Applicant: The Regents of the University of California, Oakland, CA (US)

(72) Inventors: Randolph Hastings, San Diego, CA (US); Nathan Delson, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/068,517

(22) PCT Filed: Jan. 13, 2017

(86) PCT No.: PCT/US2017/013313
§ 371 (c)(1),
(2) Date: Jul. 6, 2018

(87) PCT Pub. No.: WO2017/123852
PCT Pub. Date: Jul. 20, 2017

(65) Prior Publication Data
US 2019/0019434 A1  Jan. 17, 2019

Related U.S. Application Data

(60) Provisional application No. 62/279,148, filed on Jan. 15, 2016.

(51) Int. Cl.
*G09B 23/28* (2006.01)
*G09B 23/32* (2006.01)
*G16H 50/50* (2018.01)

(52) U.S. Cl.
CPC ............ *G09B 23/32* (2013.01); *G16H 50/50* (2018.01)

(58) Field of Classification Search
USPC .................... 434/262, 265, 267, 268, 272
See application file for complete search history.

(56) References Cited

U.S. PATENT DOCUMENTS 4,484,896 A * 11/1984 Kohnke ............... G09B 23/285
434/265
5,823,787 A    10/1998 Gonzalez et al.
(Continued)

OTHER PUBLICATIONS

PCT/US2017/013313 International Search Report and Written Opinion dated Mar. 31, 2017.
(Continued)

*Primary Examiner* — Kurt Fernstrom
(74) *Attorney, Agent, or Firm* — Wagenknecht IP Law Group, PC

(57) ABSTRACT

The adjustable airway mannequin with visual feedback models the human skull, maxilla, upper teeth, lower teeth, jaw, spine and airway mounted on a backboard. Adjustments can be made to the height of the maxilla, the height of the upper teeth, the tension and distance of the jaw movement representing mouth opening, the anterior-posterior displacement of the jaw relative to the maxilla and skull, the presence or absence of the upper teeth and lower teeth, the range of motion of the spine, and tension on the airway to mimic a variety of anatomies. The mannequin may include one or more electronic proximity and position sensors that operate through magnetic field sensing, accelerometry, and optical sensing to monitor one or more of face length, jaw length, mouth opening, jaw tension, larynx position, head height off the table, and spine mobility.

25 Claims, 14 Drawing Sheets

(56) References Cited

U.S. PATENT DOCUMENTS

| | | | | |
|---|---|---|---|---|
| 6,296,490 B1* | 10/2001 | Bowden | ............... | G09B 23/288 |
| | | | | 434/265 |
| 6,638,073 B1 | 10/2003 | Kazimirov et al. | | |
| 7,665,995 B2* | 2/2010 | Toly | .................... | G09B 23/285 |
| | | | | 434/262 |
| 10,037,716 B2* | 7/2018 | Yang | ...................... | G09B 23/32 |
| 10,242,596 B2* | 3/2019 | Simeoni | ............... | G09B 23/285 |
| 2005/0244801 A1* | 11/2005 | DeSalvo | ............... | A61B 1/267 |
| | | | | 434/262 |
| 2013/0233321 A1* | 9/2013 | Singh | ................... | A61M 16/04 |
| | | | | 128/207.15 |
| 2015/0325149 A1* | 11/2015 | Maleska-Kubick | ......................... | |
| | | | | G09B 23/288 |
| | | | | 434/265 |

OTHER PUBLICATIONS

Delson et al. "Parametrically Adjustable Intubation Mannequin with Real-Time Visual Feedback," Technical Reports, Society for Simulation in Healthcare, Jun. 2012, 7:3:183-191.

* cited by examiner

PARAMETRICALLY ADJUSTABLE AIRWAY TRAINING MANNEQUIN WITH INSTRUMENTED PARAMETER ASSESSMENT

CROSS REFERENCE TO RELATED APPLICATION(S)

This application is a US national phase application under 35 USC § 371 of international patent application no. PCT/US2017/013313, filed Jan. 13, 2017, which claims the benefit of priority under 35 U.S.C. § 119(e) of U.S. Ser. No. 62/279,148, filed Jan. 15, 2016, the entire content of each of which is incorporated herein by reference.

BACKGROUND OF THE INVENTION

Field of the Invention

The invention relates generally to airway management training and more specifically to the technical field of intubation training.

Background Information

Airway management broadly refers to medical techniques to sustain the breathing of critically ill, sedated or anesthetized patients. Intubation is a specific form of airway management that involves insertion of a tube as a conduit for breathing into the windpipe, in medical terms the trachea, or just above the vocal cords aimed at the tracheal opening. Failure at intubation can lead to dangerously low levels of oxygen, which may result in severe injury (such as brain injury, stroke, and heart attack) and/or death. The intubation procedure may be assisted by a mechanical device, such as a laryngoscope or a fiberoptic bronchoscope. Intubation procedures are not straightforward and require considerable practice to master. Furthermore, some patients have anatomic features that make airway management or intubation difficult.

Training for intubation typically occurs through practice on a large number of patients. Roughly 50 patient trials are necessary to reach a 90% success rate and a much higher number are required to develop skills with difficult patients. The need to practice on patients is a problem because intubation by a novice has a higher risk of injury or complication than intubation by an expert. Another problem with practice on patients is that intubation opportunities are infrequent in some medical specialties and those practitioners have difficulty accumulating the experience necessary to gain proficiency in such procedures. One solution would be to practice on models that mimic the human anatomy, thereby avoiding risk to patients and providing unlimited practice opportunities.

The realism and mobility of the anatomical features of current models limits the effectiveness of training intubation skills. Current models provide only one set of anatomic features, but patients present innumerable combinations of size, shape, proportion, and tissue stiffness. Thus, a novice who trains on a particular model merely learns how to intubate that particular model, but has minimal ability to transfer the learned skills to the multiplicity of anatomies in patients. Furthermore, most models approximate a normal anatomic configuration that poses no problem for intubation, so novices do not gain experience with difficult situations. Some intubation models in current use can toggle between two different settings for certain features. The SimMan intubation mannequin, for example, can vary from normal tongue size to severe swelling or from normal neck mobility to an immobile neck. Since the difficult setting makes intubation nearly impossible, the adjustments do not help novices learn how to intubate with less severe anatomic configurations that still can pose difficulty. Furthermore, practicing on only two anatomies, with one being nearly impossible, does not provide a realistic approximation of performing intubations on many different anatomies in the real world.

For training methods to be effective, students must be given feedback on their performance and how they could improve. Providing feedback for intubation is difficult because the procedure occurs within the model or patient's throat and an instructor cannot always see what the trainee is doing. Likewise, the trainee is typically unable to see how the instructor demonstrates the intubation procedure. In response to this problem, one current training system mounts a video camera on the student or instructor's head, aligned with the individual's dominant eye. The camera gives a view of what the person sees while performing the intubation procedure. However, the system still does not convey real-time information on what movements the operator is making, how much force he or she is exerting, and how the patient or model's head or neck have been moved or manipulated during the procedure.

Moreover, for proper training, motion of the neck should realistically simulate human anatomy. For example, the human spine allows for relative motion between each vertebra. Thus, the human spine cannot be accurately modeled by a single pivot as is done in some current training mannequins. Thus, a more accurate modeling of motion at each vertebra would allow for more realistic simulation of spine motion. For example, clinical practice calls for the patient's head to be placed in the "sniff position" prior to intubation, where the head is translated forward but not rotated forward or backwards. In the sniff position some vertebra are in flexion and others are in extension. This type of motion is not possible to simulate with mannequin that models neck motion with a single pivot. Accordingly, a need exists for a mannequin that can simulate human neck motion accurately, and allow for adjustability of neck and tissue stiffness to optimize training of medical practitioners.

SUMMARY OF THE INVENTION

The present invention provides an intubation training mannequin that allows multiple adjustments to each of spine rotation, mouth opening, jaw, face, teeth, and tissue stiffness. Also provided a system incorporating the mannequin that enables an instructor to monitor motions, forces and angles involved in a laryngoscopy procedure, process data obtained from a variety of sensors, and display results in real time. In various embodiments, the results may be displayed on a video screen superimposed with a representation of how experts perform the intubation.

Accordingly, the invention provides a mannequin for simulation of airway management of a human being. The mannequin includes a skull having an upper surface and a bottom surface, wherein the skull comprises an adjustable face mounted to the upper surface of the skull, adjustable upper teeth removably attached to the adjustable face, and adjustable lower teeth removably attached to a jaw, wherein the jaw is hingedly attached to the skull; a spine comprising a plurality of vertebrae, each connected to each other and having at least one tensioning hole disposed therein, a first tensioning cable disposed through each tensioning hole of each vertebra, a larynx assembly comprising a pharynx, a larynx having an upper surface and a lower surface, and a trachea, wherein the pharynx is attached to the jaw and is in contact with the spine, and the larynx is coupled to the pharynx and the trachea, a laryngeal position sensor fixedly mounted to the upper surface of the larynx, and an occipital position sensor mounted to the bottom surface of the skull, wherein a distal end of the spine is attached to the skull and a proximal end of the spine is configured for attachment to a spine mount. Each vertebra includes a pair of vertebra sides surrounding a vertebra connector, one or more pins rotatably attached to pivot holes disposed in opposing sides of the vertebra connector, and a compressible material disposed on a top surface of each vertebra side. As described herein, the pharynx is attached to the jaw and rests on the spine, the larynx is coupled to the pharynx and the trachea, a laryngeal position sensor is mounted to the upper surface of the larynx, and an occipital position sensor is mounted to the undersurface of the skull.

The mannequin may further include a spine mount attached to the proximal end of the spine. In various embodiments, the mannequin may further include a first tensioning spool attached to the first tensioning cable, wherein rotation of the first tensioning spool adjusts tension in the first tensioning cable. In various embodiments, the mannequin may further include a first worm gearbox disposed on a rear surface of the spine mount, and attached to the first tensioning spool, wherein the first worm gearbox is configured to rotate the first tensioning spool. In various embodiments, the mannequin may further include a first pivot disposed in the skull, wherein the first tensioning cable is disposed in a double-loop format and is routed around the first pivot.

In various embodiments, the spine has seven vertebrae, and may further include a second tensioning cable disposed through the tensioning holes of each of the three vertebrae at the proximal end of the spine, a second pivot disposed in fourth vertebra from the proximal end of the spine, wherein the second tensioning cable is disposed in a double-loop format and is routed around the second pivot, a second tensioning spool attached to the second tensioning cable, wherein rotation of the second tensioning spool adjusts tension in the second tensioning cable, and a second worm gearbox disposed on the rear surface of the spine mount, and attached to the second tensioning spool, wherein the second worm gearbox is configured to rotate the second tensioning spool.

In various embodiments, the mannequin may further include a plurality of tabs disposed on top and bottom surfaces of each of the vertebrae, and a plurality of springs connecting pairs of tabs disposed on adjacent vertebrae.

In various embodiments, the mannequin may further include a backboard configured to accept attachment of the spine mount, wherein the trachea extends through an opening in the backboard. Likewise, the mannequin may further include a baseboard fixedly attached to the backboard. In various embodiments, the mannequin may further include an adjustable platform disposed on the baseboard and positioned in alignment with the bottom surface of the skull, wherein the platform is configured to adjust the vertical position of the skull.

In various embodiments, the mannequin may further include an elastic band disposed over a portion of the trachea and attached to the baseboard, wherein the elastic band is configured to apply pressure to the portion of the trachea. The elastic band may be attached to the baseboard with one or more springs. The laryngeal position sensor and the occipital position sensor may be magnetic position sensors and may be configured to monitor position and rotation of the mannequin. In various embodiments, the mannequin may further include one or more resistance elements attached to the jaw and the skull, wherein the elements are configured to adjust tension of the jaw.

In various embodiments, the mannequin may further include a data acquisition means in wireless or electrical communication with each of the sensors and configured to obtain data from one or more of the laryngeal position sensor and the occipital position sensor. The data acquisition means may be further configured to obtain data from one or more sensors mounted to a device for manipulating the airway of a human. The device may be a laryngoscope having one or more of a laryngoscope position sensor and a force sensor mounted thereto. The data acquisition means may include one or more of a position sensor input box and a force sensor input box. The data acquisition means may be a computer configured to process force and position data prior to displaying the real time data to the user on a display.

In another aspect, the invention provides a training mannequin for simulation of airway management of a human being. The mannequin includes a skull having an upper surface and a bottom surface, wherein the skull comprises an adjustable face mounted to the upper surface of the skull, adjustable upper teeth removably attached to the adjustable face, and adjustable lower teeth removably attached to a jaw, wherein the jaw is hingedly attached to the skull, a spine comprising seven vertebrae, each vertebra being connected to each other and having at least two tensioning holes disposed therein, a first tensioning cable disposed through a first tensioning hole of each vertebra, a second tensioning cable disposed through a second tensioning hole of each vertebra, a larynx assembly comprising a pharynx, a larynx having an upper surface and a lower surface, and a trachea, wherein the pharynx is attached to the jaw and is in contact with the spine, and the larynx is coupled to the pharynx and the trachea, and a laryngeal position sensor fixedly mounted to the upper surface of the larynx, and an occipital position sensor mounted to the bottom surface of the skull, wherein a distal end of the spine is attached to the skull and a proximal end of the spine is configured for attachment to a spine mount. In various embodiments, each vertebra includes a pair of vertebra sides surrounding a vertebra connector, one or more pins rotatably attached to pivot holes disposed in opposing sides of the vertebra connector, and a compressible material disposed on a top surface of each vertebra side.

In various embodiments, the mannequin may further include a spine mount attached to the proximal end of the spine. In various embodiments, the mannequin may further include a first tensioning spool attached to the first tensioning cable, and a second tensioning spool attached to the second tensioning cable, wherein rotation of the first tensioning spool adjusts tension in the first tensioning cable and rotation of the second tensioning spool adjusts tension in the second tensioning cable. In various embodiments, the mannequin may further include a first worm gearbox disposed on a rear surface of the spine mount and attached to the first tensioning spool, and a second worm gearbox disposed on the rear surface of the spine mount and attached to the second tensioning spool, wherein the first worm gearbox is configured to rotate the first tensioning spool and the second worm gearbox is configured to rotate the second tensioning spool. In various embodiments, the mannequin may further include a first pivot and a second pivot disposed in the skull, wherein the first tensioning cable is disposed in a double-loop format and is routed around the first pivot and the second tensioning cable is disposed in a double-loop format and is routed around the second pivot. In various embodiments, the mannequin may further include a first spring disposed between the first tensioning cable and the first tensioning spool and a second spring disposed between the second tensioning cable and the second tensioning spool.

In another aspect, the invention provides a system for training a user to perform a laryngoscopy. The system includes the mannequin described herein, a laryngoscope having one or more of a laryngoscope position sensor and a force sensor mounted thereto, a data acquisition means for obtaining data from one or more sensors mounted to the mannequin and the laryngoscope, and a display for displaying real time data obtained from the data acquisition means to a user. In various embodiments, the data acquisition means is a computer configured to process force and position data prior to displaying the real time data to the user. In another embodiment, the system includes one or more electronic proximity and position sensors disposed on the mannequin and in electric communication with the computer, and configured to detect and monitor features of the mannequin. The one or more electronic proximity and position sensors may operate through magnetic field sensing, accelerometry, and optical sensing to monitor one or more of face length, jaw length, mouth opening, jaw tension, larynx position, head height off the table, and spine mobility.

BRIEF DESCRIPTION OF THE DRAWINGS

FIG. 17A shows a single tensioning cable in a double-loop format. FIG. 17B shows a pair of tensioning cables, each in a double-loop format for increased adjustability. FIG. 17C shows incorporation of a tabs and springs between adjacent vertebrae. FIG. 17D shows incorporation of flexion and extension tensioning cables run through through-holes disposed in side surfaces of the individual vertebra.

DETAILED DESCRIPTION OF THE INVENTION

Figure 1:
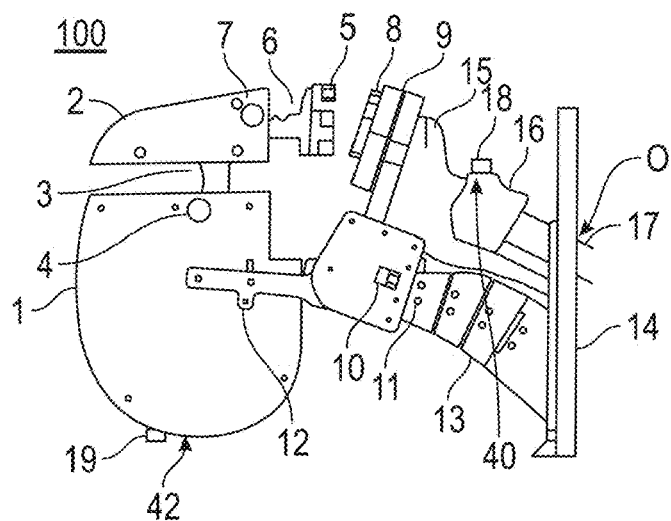
FIG. 1 is a perspective view of an exemplary embodiment of the training mannequin.

The present invention is based on airway management training and more specifically to the technical field of intubation training.

Before the present device is described, it is to be understood that this invention is not limited to the particular embodiments described, as such aspects may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the device" includes one or more devices of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention devices corresponding to the scope of each of these phrases.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described Patients can suffer from limited spine mobility due to degenerative changes, from various forms of arthritis, or from trauma. The limitations can range from a minimal reduction to complete loss of movement and can occur anywhere in the cervical spine. For example, the spine could have reduced atlanto-occipital extension, the movement involved in tilting the head back, i.e., extension. Alternatively, the vertebrae in the neck, the sub-axial cervical spine, could demonstrate limitation to flexion, i.e., movement that would tilt the chin toward the chest. Trainees must also learn techniques for successful intubation in conditions when spine mobility is abnormally reduced. The ability to assume the "sniff position" depends on proper positioning of both the atlanto-occipital joint and the sub-axial spine, but different adaptations to laryngoscopy technique are necessary to accommodate limitations in the two regions. For example, reduced sub-axial flexion can be compensated by flexion in the thoracic spine in the chest to produce a modified sniff position. On the other hand, lack of atlanto-occipital extension prevents any form of the sniff position. Intubation with this type of limitation requires the trainee to employ adjunctive maneuvers and/or equipment to accommodate.

Thus, proper training of airway intubation requires practice on a mannequin in a number of configurations to simulate real-world situations. It has been found that it can be difficult to maintain accuracy while reconfiguring a training mannequin through the diverse series of anatomies that are needed for proper training and assessment. Users must pay close attention to detail to verify that the variable structures have been configured to their desired settings given the large number of adjustable parameters included in the model. Furthermore, selecting the intended setting may not ensure the desired position in the mannequin. Thus, a mannequin must be able to model both forms of spine limitation to provide an adequate training environment.

Accordingly, the present invention provides a system to determine physical parameters of each of the adjustable features of an airway training mannequin, record the parameters, and alert the users to the configuration they are about to use for training. Exemplary adjustable features that may be monitored include, but are not limited to face length, jaw length, mouth opening, jaw tension, larynx position, head height off the table, neck stiffness and spine mobility. The system is also configured to continuously monitor the position of key anatomic structures while the trainee is performing the procedure. The continuous position data are used to properly align the trajectory of the laryngoscope and endotracheal tube with the manikin airway anatomy. Otherwise, if these adjustments were not made, the software would assume that the laryngoscope and tube were moving through a standard, fixed passage that in all likelihood would bear little resemblance to the actual location of the mouth, pharynx, vocal cords, larynx and trachea. This inaccuracy would negate the feedback value of the trajectory tracking system.

The system and mannequin described herein thus provides an automated assessment and recordation of the anatomic configuration of the training mannequin before the procedure starts, and tracks the laryngoscope and endotracheal tube trajectory, which are aligned correctly with the anatomic structures regardless of which of the 300 or more configurations are selected. As such, the system is configured to reproduce the specific anatomic configurations necessary for optimal training, which can be difficult if based just on a visual assessment. Additionally, to compensate for the calibration between the physical settings and the actual position of the mannequin changing with time and use, the system is configured to self-calibrate thereby eliminating such variances. Further, the positions of each of the mouth, pharynx, larynx and vocal cords can be varied appreciably amongst the different configurations to simulate a variety of anatomical differences. Those shifts must be taken into account to provide healthcare students with accurate feedback about whether they are performing the procedure properly.

Referring now to FIGS. 1, 6-8, 9 and 18A-18B, there is shown a side view of the mannequin (100) including skull (1), face (2), upper teeth (5), lower teeth (8), jaw (9), spine (13), backboard (14) to which the lower end of the spine (13) is connected, laryngeal position sensor (18), occipital position sensor (19) and a larynx assembly comprised of pharynx (15), larynx (16) and trachea (17). In one embodiment, the larynx assembly is a one-piece unit obtained from a manufacturer, such as Laerdal (Wappinger Falls, N.Y.), or may be a unit specifically designed to provide training in intubation techniques for specific laryngeal problems, including airway tumors, supraglottic stenosis, subglottic stenosis, edema, airway secretions, and others. The pharynx (15) is attached to the jaw (9) and rests on the spine (13). The trachea (17) extends through an opening (O) in the backboard (14), fixing the larynx assembly in place on the lower end. The larynx (16) connects pharynx (15) and trachea (17). A laryngeal position sensor (18) rests on (or is in contact with) the upper surface (40) of the larynx (16), while the occipital position sensor (19) is fixed to the bottom surface (42) of the skull (1). In one embodiment, the laryngeal position sensor (18) and the occipital position sensor (19) are miniBird Model 800 magnetic position sensors (Ascension Technology Corp, Buffington, Vt.) with six degrees of freedom (position plus rotation in 3D). A notched facial arm (3) connects the face (2) to the skull (1).

A facial adjusting means (4), such as a facial knob and pin, is inserted through the skull (1) and locks the notched facial arm (3) into position at one of the notches, thereby fixing facial height. In use, the facial adjusting means (4) can therefore be pulled laterally to release the notched facial arm (3) and allow it to be repositioned to one of the other notches, thereby allowing the height of the face (2) to be adjusted. In various embodiments, two, three, four, or five discrete heights may be available for facial adjustment. An upper teeth notched arm (6) connects the upper teeth (5) to the face (2). An upper teeth adjusting means (7), such as an upper teeth knob and pin, may be used to adjust maxillary height (i.e., the height of the upper teeth (5)), similar to the mechanism involving the facial notched arm (3) and facial adjusting means (4). The lower teeth (8) are attached to the jaw (9) with a peg such that the lower teeth (8) can be removed to model a patient missing its lower teeth (8). Similarly, the upper teeth (5) can be removed. Exemplary materials from which each of the recited components may be formed include, but are not limited to, plastics, metals, wood, and any suitable rigid material.

Figure 2A:
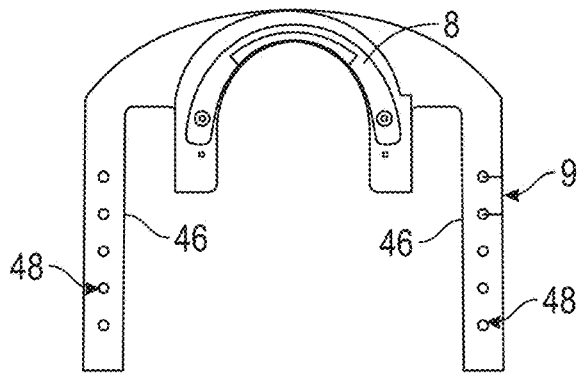
FIG. 2A is a top view of an exemplary embodiment of the jaw of the mannequin with lower teeth disposed thereon.
Figure 2B:
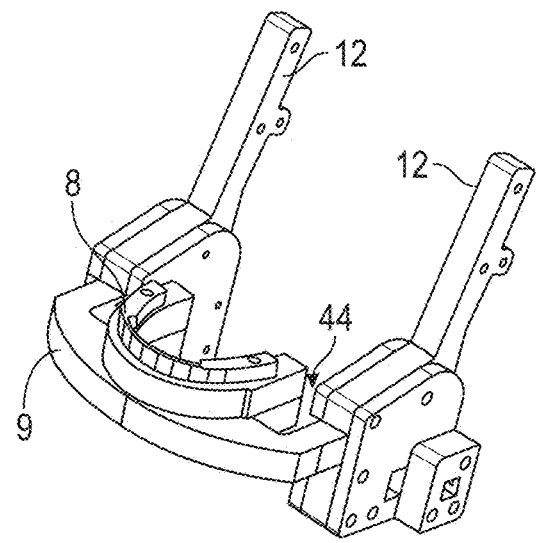
FIG. 2B is a perspective view of an exemplary embodiment of the jaw with lower teeth.

Two upper mandible arms (12) are attached to the right and left sides of the skull (1) by a pin (see FIGS. 2A and 2B). In various embodiments, each upper mandible arm (12) may include a channel (44). The right and left arches (46) of the jaw (9) pass through the respective channels (44) of the upper mandible arm (12) for adjustable attachment thereto. Thus, the upper mandible arms (12) connect the jaw (9) to the skull (1). In various embodiments, a resistance element (10) may be attached to span screws in the arch on the right side of the jaw (9) and the right upper mandible arm (12). Similarly, an identical resistance element (10) may be attached to span screws in the left arch of the jaw (9) and left upper mandible arm (12). The two resistance elements (10) can be stretched to shorter or longer lengths to adjust the tension for opening the jaw (9) and the two upper mandible arms (12). Exemplary resistance elements include, but are not limited to, springs, rubber bands, neoprene material, and silicone material.

As shown in FIG. 2A, the jaw (9) includes lower teeth (8) disposed thereon. Each of the ends of the jaw (9) constitute the above-mentioned arches (46) that slide through channels (44) in the upper mandible arms (12), shown in FIG. 1 (see also FIG. 2B). Tapped holes in the arch of the jaw (9) on each side allow differing degrees of stretch on the resistance elements (10).

Figure 3:
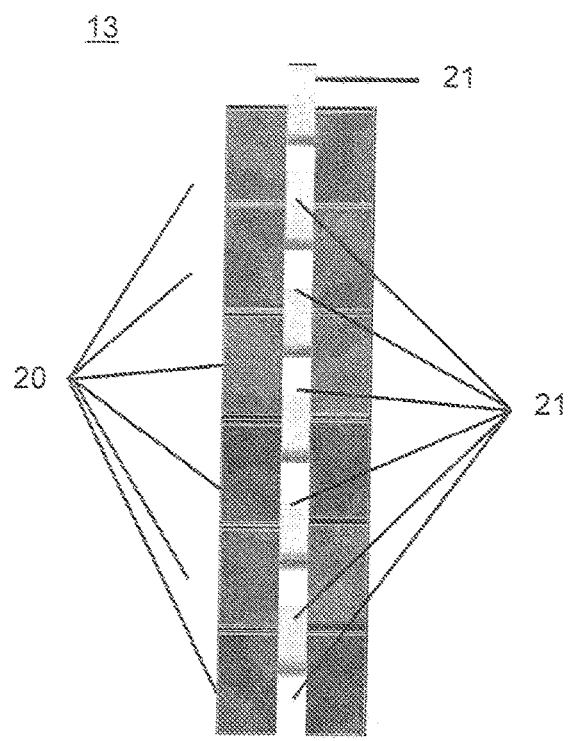
FIG. 3 is a top view of an exemplary embodiment of the spine of the mannequin.

Referring to FIG. 3, there is shown a top view of an exemplary spine assembly (13), consisting of vertebrae (20) and links (21) between the right sides and left sides of the vertebrae (20). Each vertebra (20) is matched by another vertebra (20), one on the left and one on the right. A vertebra connector/link (21) joins the paired vertebra sides (20a and 20b). Furthermore, the vertebra connector/link (21) spans a lower pair and an upper pair of vertebrae (20). Each the lower pair of vertebrae are joined to the vertebra connector (21) by two screws on the upper end of the respective vertebrae (20), as shown. In various embodiments, the vertebra connector/link (21) may be formed in a triangular shape, with the longest triangle limb containing the holes for the aforementioned screws. The upper pair of vertebrae (20) are joined to the vertebra connector/link (21) by a single screw through the vertex of the triangle. Tensions on the screws, vertebrae (20) and vertebra connectors/links (21) may all be adjusted to provide an anatomic range of motion at each vertebral level.

Figure 4A:
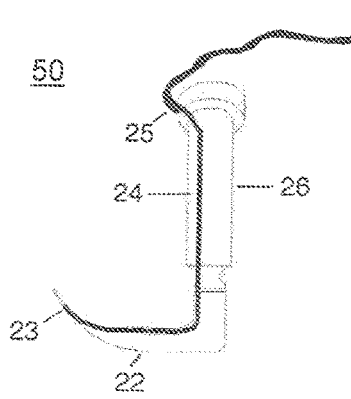
FIG. 4A is a pictorial diagram of an exemplary embodiment of the laryngoscope of the system with position sensor, force sensor assembly and sensor cables.
Figure 4B:
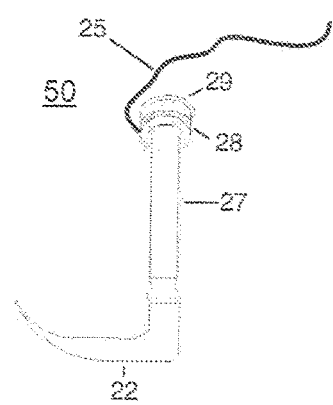
FIG. 4B is a pictorial diagram of an exemplary embodiment of the internal shaft of the laryngoscope of FIG. 5 showing the force sensor.

Referring to FIG. 4A, there is shown a perspective view of an instrumented laryngoscope (50) for use in the training system. The laryngoscope (50) includes a blade (22), laryngoscope position sensor (23), position sensor cable (24), force sensor cable (25), and shell (26). The blade (22), produced commercially and purchased for use in the device, is attached the laryngoscope shaft (27), which is inside the shell (26). The laryngoscope shaft (27) is illustrated in FIG. 4B. In various embodiments, the laryngoscope position sensor (23) may be attached to the laryngoscope at any suitable location from the intersection of the blade (22) with the handle to the tip of the blade (22). The position sensor cable (24) runs under the blade (22), then up the shell (26) to its input box (not shown). The force sensor cable comes out of the side of the shell (26) also goes to its input box (not shown). The force sensor cable (26) also supplies power to the force sensor (28) and to a light bulb (not shown) on the blade (22). In various embodiments, the force sensor (28) may be disposed inside the shell (26), for example, at the upper lingual surface of the blade or on the lower surface of the blade.

Referring now to FIG. 4B, the laryngoscope shaft (27) is shown with the shell (26) removed, thereby exposing the force sensor (28) and load transfer plate (29). The laryngoscope shaft (27) is attached to the blade (22) at one end. The opposite end of the laryngoscope shaft (27) is mounted with the force sensor (28), which connects via the load transfer plate (29) to the shell (26).

Figure 5:
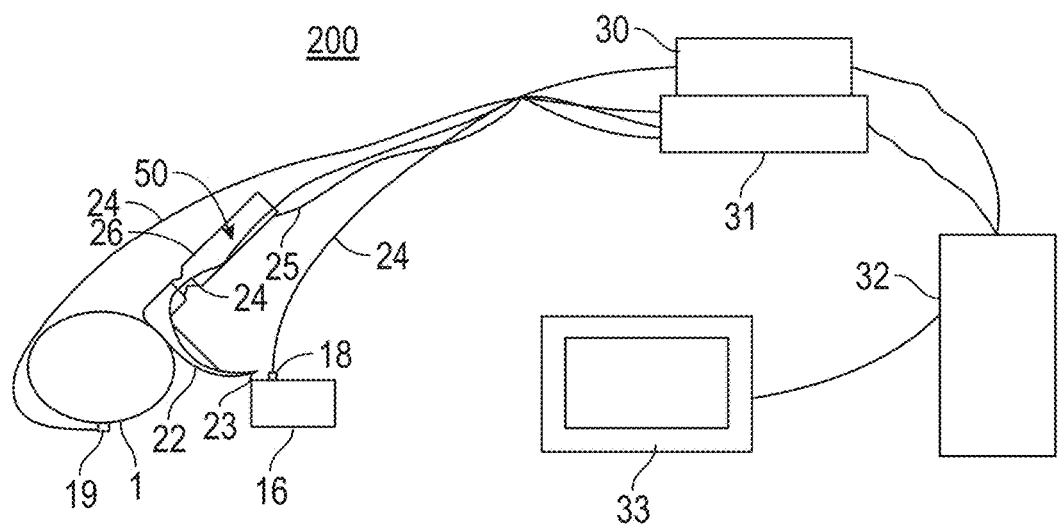
FIG. 5 is a pictorial diagram showing the organization of the components of the adjustable airway mannequin system with visual feedback.

Referring now to FIG. 5, there is shown an organizational diagram of the components of the system (200). The system (200) includes the mannequin (100), occipital position sensor (19), laryngeal position sensor (18), position sensor cables (24), laryngoscope (50), laryngoscope position sensor (23), force sensor cable (25), force sensor input box (30), position sensor input box (31), computer (32), and display (33). Laryngoscopy may therefore be performed with the instrumented laryngoscope (50). Position data are generated for the laryngoscope (50), laryngoscope position sensor (23), laryngeal position sensor (18) and occipital position sensor (19). These data are transmitted through position sensor cables (24) to the position sensor input box (30/31). Laryngoscope force is measured by the force sensor (not shown) and transmitted through the force sensor cable to the force sensor input box (not shown) or directly to the computer (32). Force and position data may then be processed at the respective input boxes or at the computer (32), analyzed and presented as a real time display on the display (33) as feedback for the student performing laryngoscopy.

In various embodiments, the system (200) may be configured for wireless communication, such as one-way or two-way transmission of information, between the mannequin, laryngoscope, and/or one or more electronic devices selected from the group consisting of a mobile device, a personal computer, and a display. Thus, instead of, or in addition to, the wired connectivity between the laryngoscope position sensor (23), force sensor cable (25), force sensor input box (30), position sensor input box (31), computer (32), and display (33), any of these connections may be in wireless format.

Exemplary mobile devices include, but are not limited to, a cellular phone, a tablet computer, a laptop computer, or a wireless remote controller. When configured for wireless communication, the system (200) may include a transceiver (not shown) that operates in conjunction with a communication standard such as 802.11, Bluetooth, ZigBee, ultra-wideband, GPS, Wi-Fi, Wimax, GPS, radio frequency, or other standard short or medium range communication protocol, or other protocols to send/receive information from any of the disclosed sensors for training purposes. Alternatively, or in addition thereto, the transceiver may be configured for direct mobile telephony (i.e., cellular networks) for streaming imaging data from one or more cameras disposed in various locations of the mannequin for supervised training of medical practitioners.

Accordingly, the system (200) disclosed herein is configured to assess the positions of various components of the model with electronic proximity and position sensors during intubation training. In various embodiments, the sensors work through magnetic field sensing, accelerometry, optical or other means. Spine and mouth tension may be assessed by applying calibrated weights onto the spine and using an accelerometer to determine spine orientation.

Figure 6:
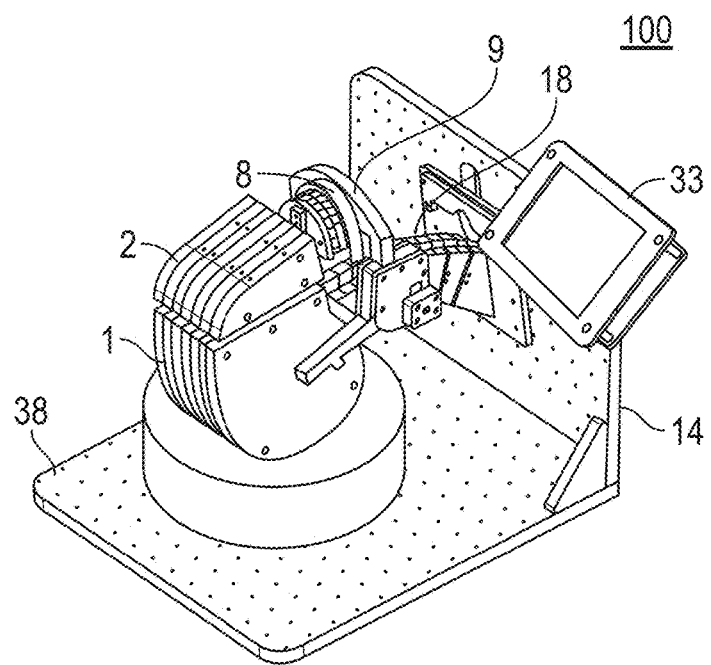
FIG. 6 is a pictorial diagram of an exemplary embodiment of the mannequin model mounted to the backboard with a display monitor for real time user feedback.
Figure 7:
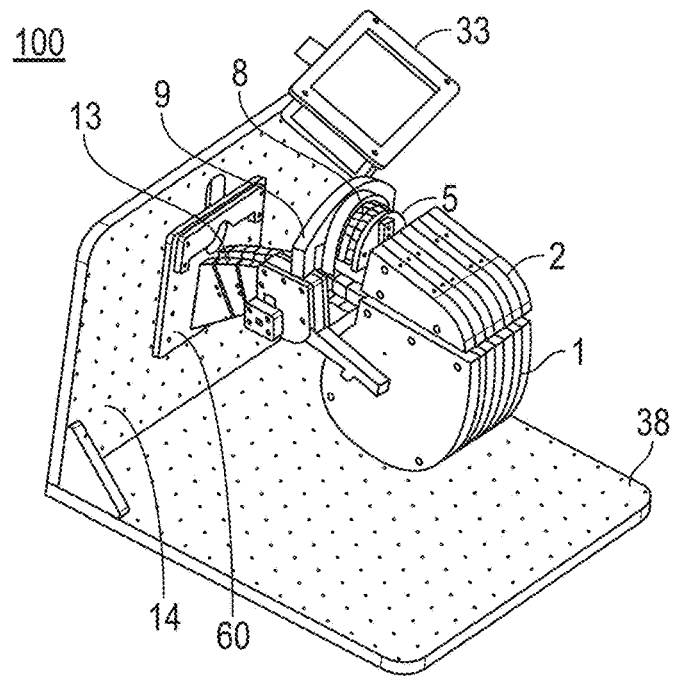
FIG. 7 is a pictorial diagram showing a perspective view of an exemplary embodiment of the training system with mannequin model mounted to the backboard and the display monitor for real time user feedback.
Figure 8:
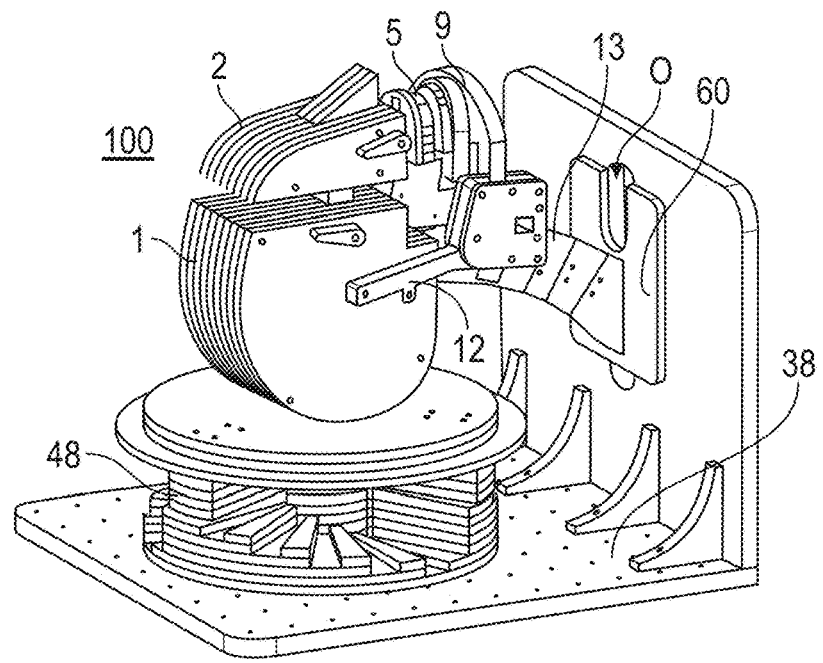
FIG. 8 is a pictorial diagram showing a perspective view of another exemplary embodiment of the training mannequin with adjustable components.

Referring now to FIGS. 6-8, there are shown various perspective views of the mannequin (100). As discussed above with reference to FIG. 1, the mannequin (100) includes a skull (1), face (2), upper teeth (5), lower teeth (8), jaw (9), spine (13), backboard (14) to which the lower end of the spine (13) is connected, laryngeal position sensor (18), occipital position sensor (19) and a commercial larynx assembly comprised of pharynx (15), larynx (16) and trachea (17). As discussed above, various embodiments of the mannequin (1) include an adjustable mandible, adjustable upper incisors, adjustable lower mandible, adjustable pillow/platform, and a spine that is adjustable for stiffness, to allow for training of a greater pool of human beings with variations to their facial features. In certain embodiments, the mannequin (100) may further include a height-adjustable pillow/platform (48) disposed on a baseboard (38) and positioned in alignment with the base of the skull (1). In use, the height-adjustable pillow/platform (48) may be rotated into any of predetermined heights to allow the trainee to adjust the vertical position of the head prior to laryngoscopy.

Figure 9:
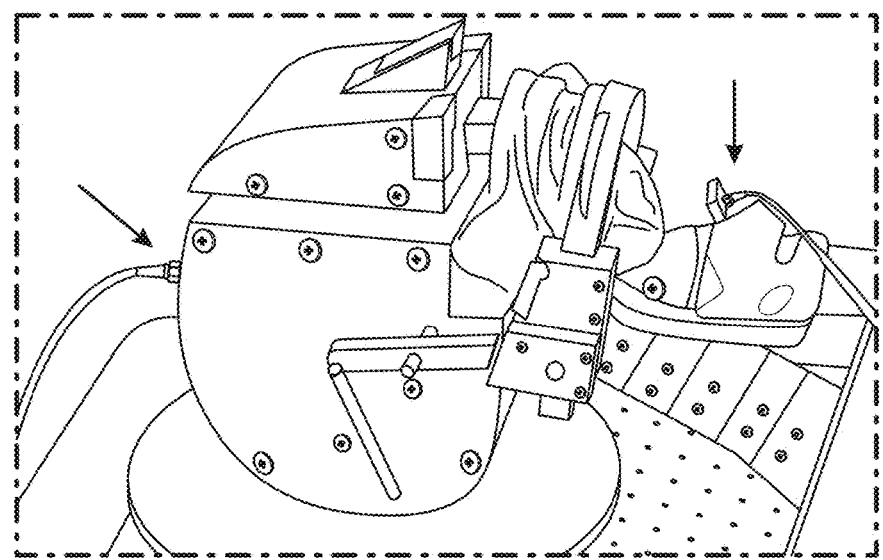
FIG. 9 is a pictorial diagram of a side perspective view of the training system showing sensors attached to the mannequin (white arrows).

As shown in FIG. 9, sensors (18, 19, denoted by white arrows) are attached to the mannequin (100) to track both the position of the mannequin during laryngoscopy. In various embodiments, the mannequin (100) may include one or more additional sensors (not shown) configured to detect the face length, the pillow/platform height, the jaw length and subluxation, spine stiffness, and spine movement. Thus, any movement of the mannequin (100) during the procedure must be considered in order to position the trajectory correctly. Additionally, any adjustments to face length, jaw length, pillow/platform height or subluxation must also be taken into account.

In another aspect, the invention provides a mannequin (100) further configured to provide the ability to adjust neck stiffness. By adding the ability to adjust neck stiffness, a wider range of patient anatomies can be simulated.

Figure 10:
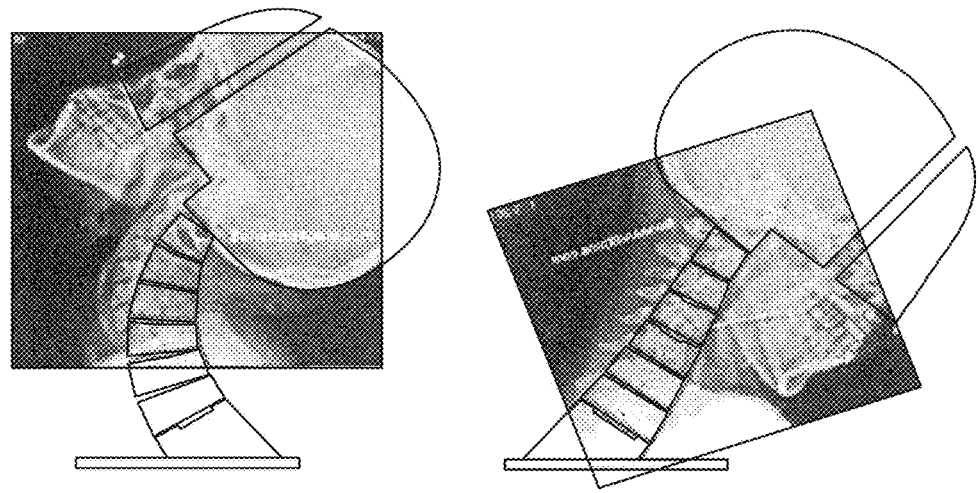
FIG. 10 is a pictorial diagram of an X-ray of a human spine in flexion and extension with the mannequin spine geometry superimposed thereon.

Motion of the spine is important in medical procedures such as airway intubation via laryngoscopy. Patients with stiff spines are known to be difficult to intubate. Accordingly, it is important that medical practitioners be able to train on mannequins that can simulate a wide range of neck stiffness's. For airway intubation, the primary motion of the neck is in the sagittal plane. The human spine articulates in flexion and extension in the sagittal plane through motion of one vertebra relative to the adjacent vertebra. The motion between two vertebrae can be approximated by rotation about a pivot. Accordingly, the spine of the mannequin (100) disclosed herein was designed with vertebrae that pivot relative to each other. For the purposes of the intubation training mannequin (100), the cervical spine (13) may be provided with vertebrae C1-C7. FIG. 10 shows an X-ray of a human spine in flexion and extension with the mannequin spine geometry superimposed.

Figure 11A:
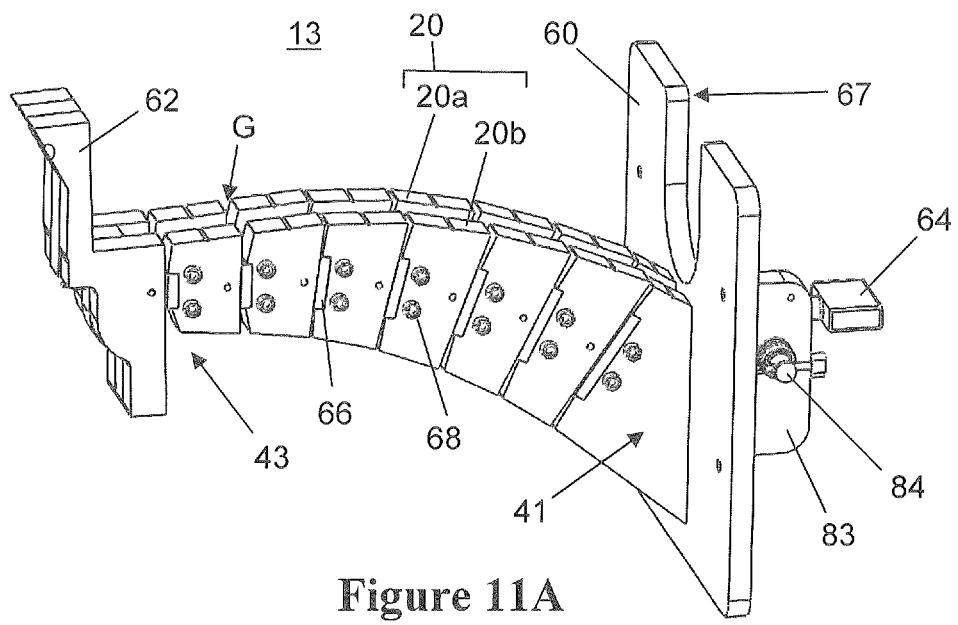
FIGS. 11A and 11B are perspective views of an exemplary embodiment of the adjustable spine of the mannequin.
Figure 11B:
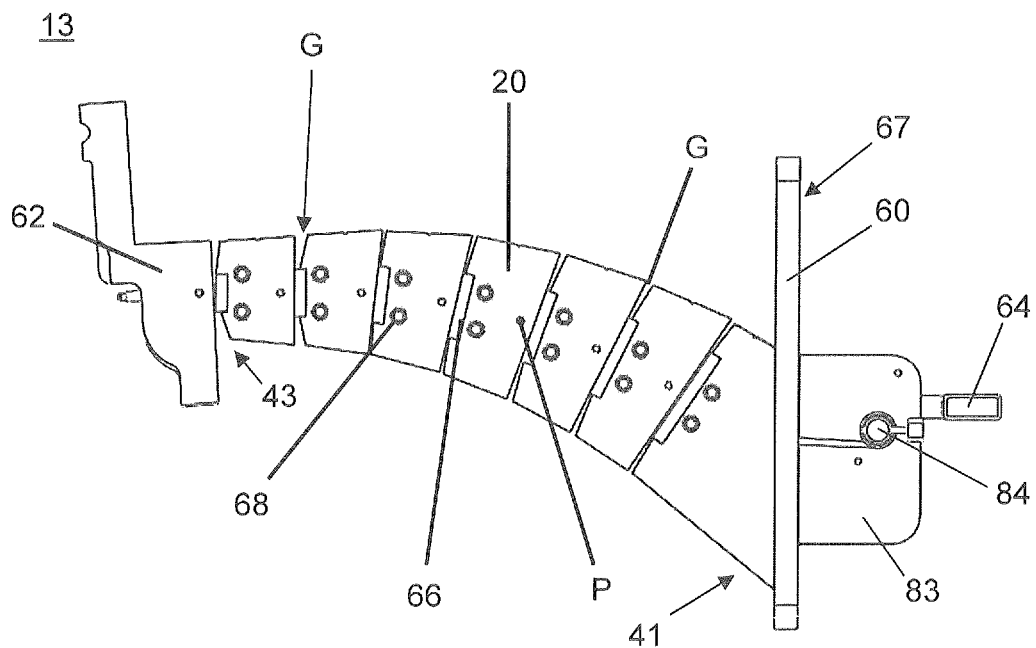

Referring now to FIGS. 11A and 11B, an exemplary embodiment of the spine (13) with adjustable stiffness is shown. As described above, the spine (13) includes individual vertebrae (20) and has a proximal end (41) and a distal end (43) relative to the trainee. A spine mount (60) attaches the spine (13) to the backboard (14) and a portion of the skull (62) is configured to attach the spine (13) to the skull (1). In various embodiments, a worm gearbox (64) may be disposed on a rear surface (67) of the spine mount (60) and configured to adjust spine stiffness, as described in more detail below. As shown in FIG. 11B, there are gaps (G) are provided between each vertebra (20). The vertebrae (20) pivot relative to each other at the pivots points (P) shown. In various embodiments, a compressible material (66) is disposed between each vertebra (20) and configured to hold the vertebrae snug relative to each other. In certain embodiments, the compressible material (66) is foam rubber or silicone. Assembly screws (68) hold each individual vertebra together, as discussed in further detail below.

Figure 12A:
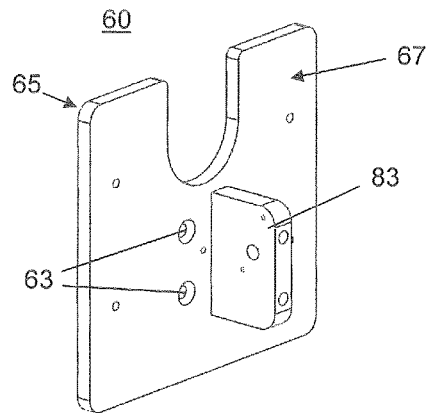
FIGS. 12A-12C are pictorial diagrams showing assembly of an exemplary embodiment of the spine mount (FIG. 12A), installation of the worm gearbox (FIG. 12B), and the completed spine mount assembly (FIG. 12C).
Figure 12B:
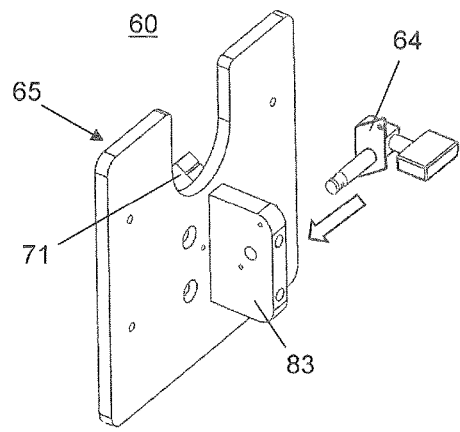
Figure 12C:
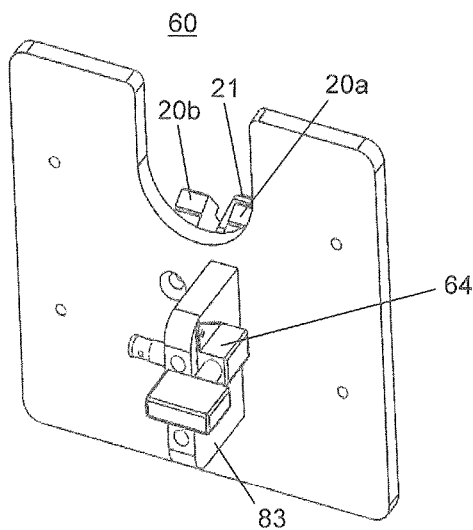

Referring now to FIGS. 12A-12C, the spine mount (60) is configured to hold the spine (13) in place and connect the mannequin (100) to the backboard (14), simulating the body of a patient. As shown in FIG. 12A, the spine mount (60) includes a plurality of mounting holes (63) disposed therein for attaching to a backboard (14) of the system (200). Fixedly disposed on the rear surface (67) of the spine mount (60) is a gearbox mount (83) extending away from the plane of the rear surface (67) of the spine mount (60). As shown in FIG. 12B, worm gearbox (64) is inserted into the gearbox mount (83), resulting in a worm gearbox (64) configured to tighten a cable similar to the tuning pegs of a guitar. Disposed on the front surface (65) of the spine mount (60) is a spine attachment (71) configured for pivotal attachment to the proximal vertebra (20) of the spine (13). In various embodiments, the spine attachment (71) may be shaped in accordance with the vertebra connector (21), as described below, to facilitate attachment of the vertebrae (20) thereto. FIG. 12C shows a completed spine mount (60) with a completed vertebrae (20) attached thereto. In various embodiments, a tightening spool (84) may be fixedly attached to the worm gearbox (64) such that rotation of the worm gearbox (64) causes the tightening spool (84) to rotate in the desired direction. Tightening spool (84) is configured to accept one or more tightening cables (80, 81) to be wound thereupon, as discussed in further detail below.

Figure 13:
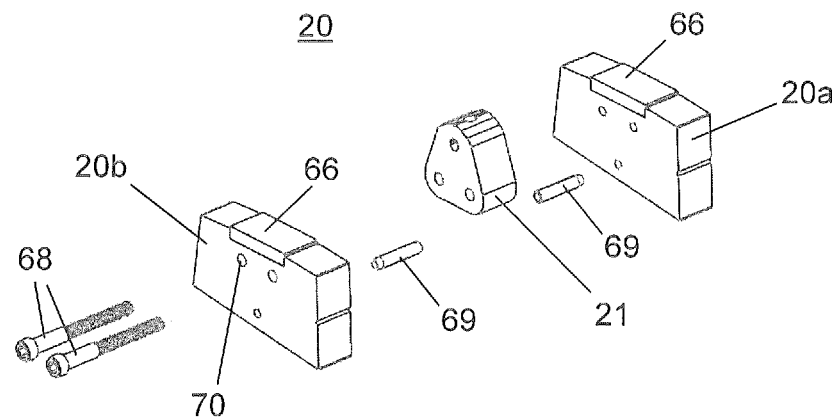
FIG. 13 is an exploded view of an exemplary embodiment of a single vertebra of the spine of the mannequin.

Referring now to FIG. 13, construction of a single vertebra (20) is shown in an exploded view. Each vertebra (20) is constructed with a right (20a) and left side (20b). In the center is a link or vertebra connector (21). A pin (69) serves as a pivot between the adjacent vertebra and passes through the right (20a) and left (20b) sides of the vertebra as well as the vertebra connector (21). The compressible material (66) is placed between adjacent vertebrae to hold the vertebrae snug relative to each other and to provide a restorative force to hold the neck of the mannequin (100) in a neutral position. Assembly screws (68) hold the vertebrae (20a, 20b) sides together.

Figure 14A:
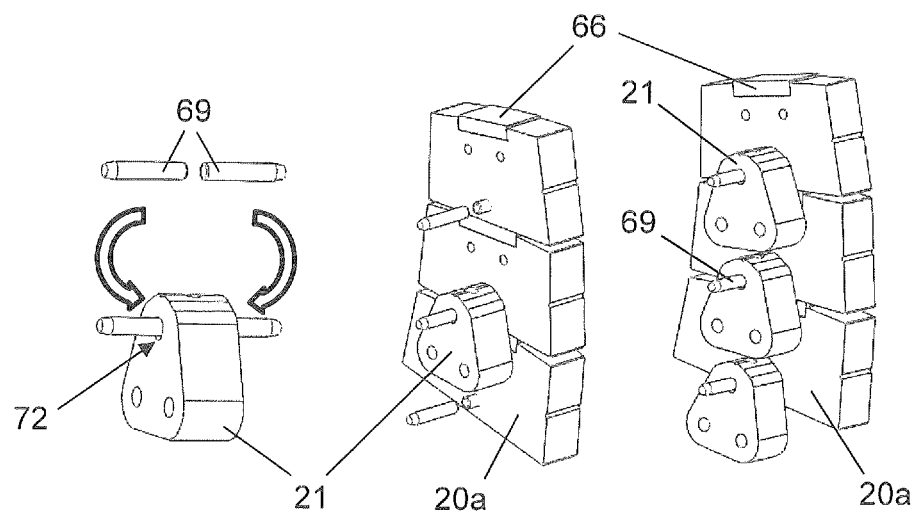
FIGS. 14A-14C are pictorial diagrams showing assembly of an exemplary embodiment of the spine of the mannequin (FIG. 14A), a fully assembled vertebra (FIG. 14B), and a pair of assembled vertebrae (FIG. 14C).
Figure 14B:
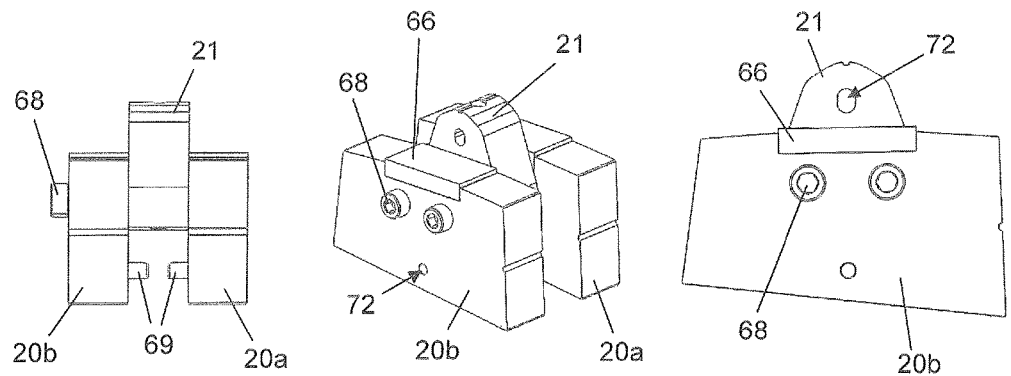
Figure 14C:
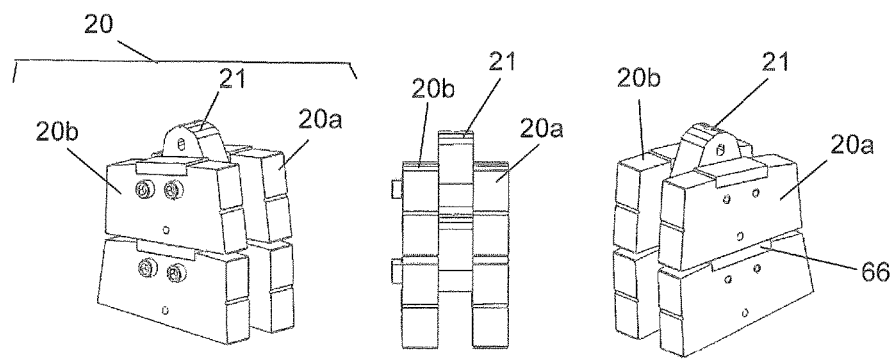

As shown in FIG. 14A, assembly of the spine (13) proceeds by inserting first ends of each of a pair of pins (69) into opposing pivot holes (72) of a vertebra connector (21). The second end of one of the pins (69) is then inserted into a corresponding pivot hole (72) of either the right (20a) or left side (20b) of the vertebra (20). For illustrative purposes only, the pivot pin (69) is inserted into the right side (20a) of the vertebra (20). The compressible material (66) is then placed into the corresponding slot on the top surface of the right side (20a) of the vertebra. This step is continued until a chain of vertebra connectors (21) and right sides (20a) of the vertebrae has been created with pins (69). As shown in FIG. 14B, the left sides (20b) of each corresponding right side (20a) of the vertebrae are then fit over the protruding pin (69) from each vertebra connector (21) and a pair of assembly screws (68) is screwed into the respective holes (70) for assembly. FIG. 14C shows various perspective views of a pair of adjacent vertebrae (20) connected together following assembly.

Figure 19A:
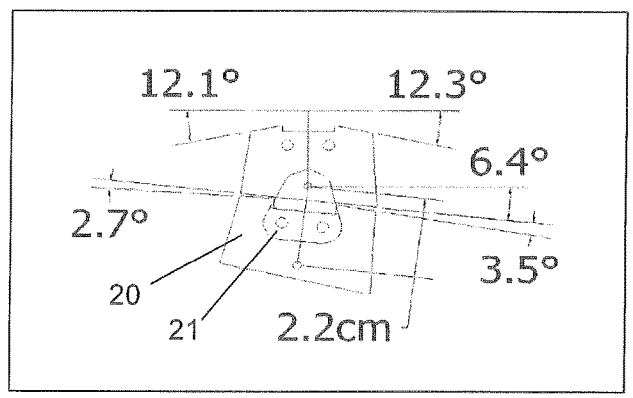
FIGS. 19A and 19B are pictorial diagrams showing the relative motion between an exemplary embodiment of the vertebra (FIG. 19A) and the range of possible spine stiffnesses (FIG. 19B).

The relative motion between adjacent vertebrae is based upon the geometry of the vertebra and the pivot location, as shown in Table 1. In embodiments where the pivot (P) is in a fixed location, the relative motion between adjacent vertebrae (20) is fixed. The relative motion between vertebrae (20) is exemplified in FIG. 19A. As shown, the gap between the vertebrae determines the relative amount of rotation between the vertebrae. For example, there is up to 2.7 degrees of extension and 3.5 degrees of flexion between the vertebrae (20) in this configuration. If the gap between the two vertebrae is increased, even more rotation will be allowed before the edges of the vertebrae bump into each other to limit the range of motion.

TABLE 1

| | Panjabi et al. [1] | | | | Harrison et al. [2] | | Mannequin |
|---|---|---|---|---|---|---|---|
| Joint | Flexion (f) | | Extension (b) | | Between Axis | | Length (cm) |
| C0-C1 | 7.2 | ±2.5 | 20.2 | ±4.8 | | | 2.2 |
| C1-C2 | 12.3 | ±2.0 | 12.1 | ±6.5 | | | 2.2 |
| C2-C3 | 3.5 | ±1.3 | 2.7 | ±1.0 | 6.4 | ±5.4 | 2.2 |
| C3-C4 | 4.3 | ±2.9 | 3.4 | ±2.1 | 6.9 | ±5.1 | 2.2 |
| C4-C5 | 5.3 | ±3.0 | 4.8 | ±1.9 | 6.8 | ±5.0 | 2.2 |
| C5-C6 | 5.5 | ±2.6 | 4.4 | ±2.8 | 6.6 | ±5.3 | 2.2 |
| C6-C7 | 3.7 | ±2.1 | 3.4 | ±1.9 | 7.8 | ±6.0 | 2.2 |

Figure 15A:
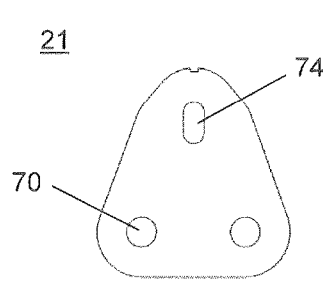
FIGS. 15A and 15B are pictorial diagrams showing a single vertebra connector with an elongated slot (FIG. 15B) for added adjustability, and tensioning holes disposed therethrough (FIG. 15C).
Figure 15B:
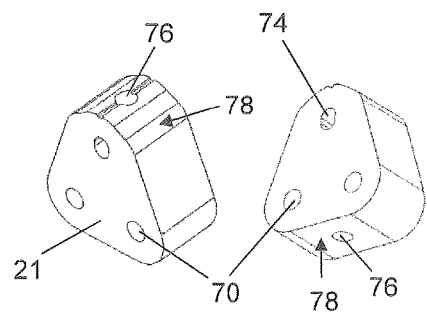

In order to provide adjustable spine stiffness, the vertebra connectors (21) may be provided with a slot (74) in place of the pivot hole (72) configured to allow the pivot position to vary, as shown in FIG. 15A. The slot allows the pivot position (P) between adjacent vertebrae (20) to move up and down as necessary. In various embodiments, one or more tensioning holes (76) are disposed through a side surface (78) of each of the vertebra connectors (21), as shown in FIG. 15B. A tensioning cable (80) may then be routed through the tensioning holes (76) of each adjacent vertebra connector (21).

Figure 16A:
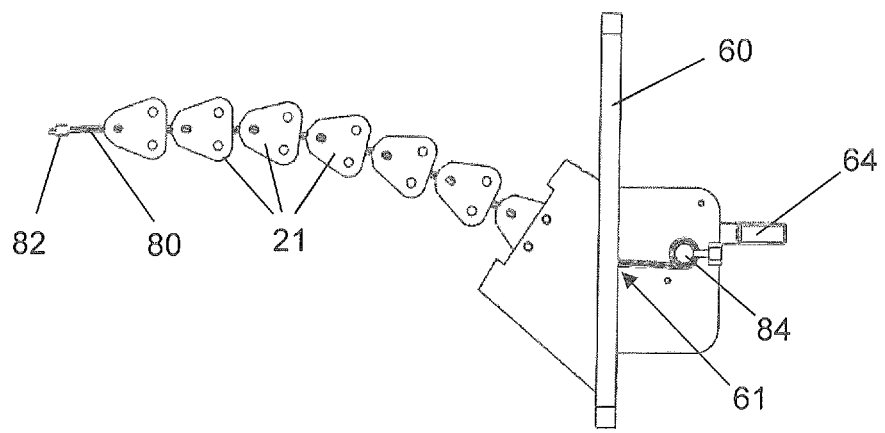
FIGS. 16A and 16B are pictorial diagrams showing a side view cross section of the spine with tensioning cable (FIG. 16A), and a close-up perspective view of the top vertebrae connectors with cable termination at the skull attachment point (FIG. 16B).
Figure 16B:
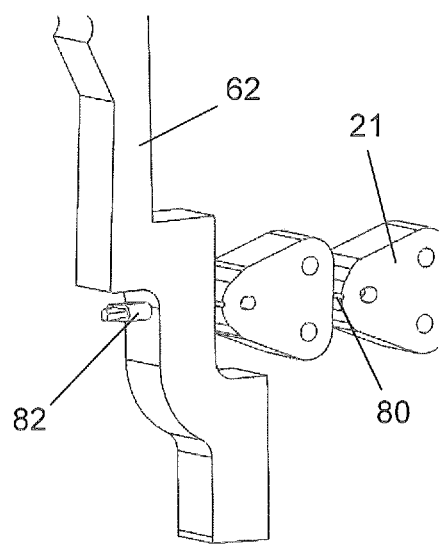

Referring now to FIG. 16A, an assembly of vertebra connectors (21) is shown relative to the exemplary embodiment of the spine (13) shown in FIG. 11B. It should be understood that in FIG. 16A, the spine is shown without the vertebrae sides for illustrative purposes only. As shown, a tensioning cable (80) is routed through each successive vertebra connector (21) and a first end is terminated at the skull (see FIG. 16B) with a cable terminator (82). The second end of the tensioning cable (80) is routed through a through-hole (61) in the spine mount (60) and is wound around a tightening spool (84) that is rotatably connected to the worm gearbox (64). Through-hole (61) may be disposed in the spine mount (60) in any location so as to minimize abrasion and wear on the tensioning cable (80) through continued use of the mannequin (100) (see FIGS. 17A-17C). In various embodiments, the tensioning cable (80) may be any flexible cable having a relatively high tensile strength, such as a steel cable or a polyethylene cable, for example, an ultra-high-molecular weight polyethylene rope marketed under the tradename DYNEEMA® (DSM Dyneema LLC, Stanley, N.C.). A completely assembled exemplary spine (13) is shown in FIG. 11A.

As the cable is tightened, the vertebrae (20) are squeezed closer together, and the gaps (g) between the vertebrae (20) are reduced. Thus, as the tensioning cable (80) is tightened the vertebrae (20) can still rotate relative to each other, but the range of rotation between each vertebra (20) is reduced. In this fashion, the range of motion of the spine (13) can be adjusted by adjusting the tension of the tensioning cable (80).

Figure 17A:
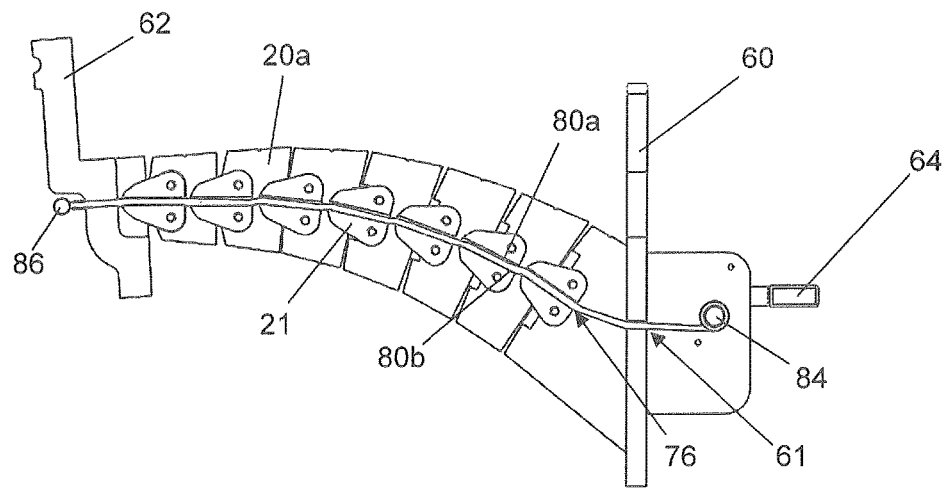
FIGS. 17A-17D are pictorial diagrams showing various exemplary side cross sectional views of the spine with adjustability of spine tension.

In certain embodiments, it may be desirable to be able to stiffen a portion of the simulated spine (13), while leaving other portions of the spine (13) in a more flexible state. For example, some patients may have heads that tilt backwards (i.e., reduced atlanto-occipital extension), or necks that tilt the chin forward (i.e., flexion of the sub-axial cervical spine). Accordingly, to simulate such anatomical differences, the spine (13) may include one or more additional tensioning cables (80) for stiffening some vertebrae (20) more than others. As shown in FIG. 17A, the spine (13) may include two tensioning cables (80a and 80b), or alternatively, a single tensioning cable (80) disposed in a double-loop format (i.e., a single cable is run through each of the vertebra connectors (21), looped around a pivot (86) and then run back through each of the vertebra connectors (21)). It should be understood that FIG. 17A shows a single side of the vertebrae (e.g., right side 20a) only with the respective vertebra connectors (21) for illustrative purposes only.

When present in a double-loop format, the tensioning cable (80a, 80b) leaves the tightening spool (84) that is rotatably connected to the worm gearbox (64), and runs through each of the vertebra connectors (21). The tensioning cable (80a, 80b) then wraps around a pivot (86) disposed at the top of the spine (13) (i.e., at the occiput which is also referred to as the C0 vertebra) at the portion of the skull (62), and runs through each of the vertebra connectors (21) through the same tensioning holes (76) or through a second tensioning hole disposed within each of the vertebra connectors (21), back to the tightening spool (84). In this configuration, the tension load is split between each of the double cables (80a, 80b), thereby strengthening the overall tensile strength of the tensioning cable (80). Since this configuration incorporates pivot (86) at the portion of the skull (62), a cable terminator (82) is not required. However, in embodiments where two independent tensioning cables (80a, 80b) are utilized, each cable may include the same cable terminator (82) or may include an independent cable terminator (82). Additionally, should the tensioning cable (80a, 80b) break through continued use, it is possible to use the end of the broken tensioning cable (80a, 80b) to pull a replacement tensioning cable (80a, 80b) through each vertebra connector (21) without the need to disassemble the spine (13).

Figure 17B:
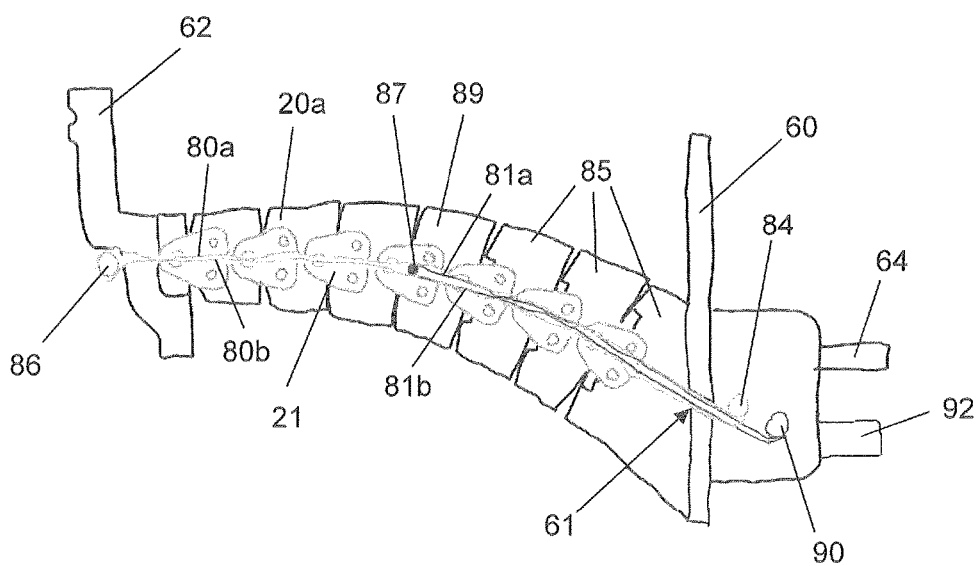

Likewise, it may be desirable to incorporate the ability to bias the direction of vertebrae motion in either flexion or extension. Accordingly, as shown in FIG. 17B, the spine (13) may include a first tensioning cable (80a, 80b), as described with reference to FIG. 17A, and a second tensioning cable (81a, 81b). In various embodiments, the second tensioning cable (81a, 81b) runs through the vertebra connectors (21) of the lower vertebrae (85) and loops around a second pivot (87) at a mid-level vertebra (89), e.g., the fourth vertebra (20) from the proximal end (41) of the spine (13). The ends of the second tensioning cable (81a, 81b) are then run through the through-hole (61) in the spine mount (60) and is wound around a second tightening spool (90) that is rotatably connected to a second worm gearbox (92). As described above, the first tensioning cable (80a, 80b) tightens all of the vertebrae (20) of the spine (13), while the second tensioning cable (81a, 81b) is configured to tighten motion of the lower vertebrae. Accordingly, when so provided, a different tension may be provided to the upper and lower vertebrae of the spine (13). For example, a low tension may be applied to the first tensioning cable (80a, 80b), while an additional tension may be applied to the lower vertebrae (85), thereby simulating a significant reduction in the range of motion of the lower vertebrae. While not shown, it is contemplated that a third, fourth, fifth, etc., tensioning cable (80) may be provided in the spine (13) to independently stiffen smaller groups of vertebrae (20) for increased adjustability of neck stiffness.

Figure 17C:
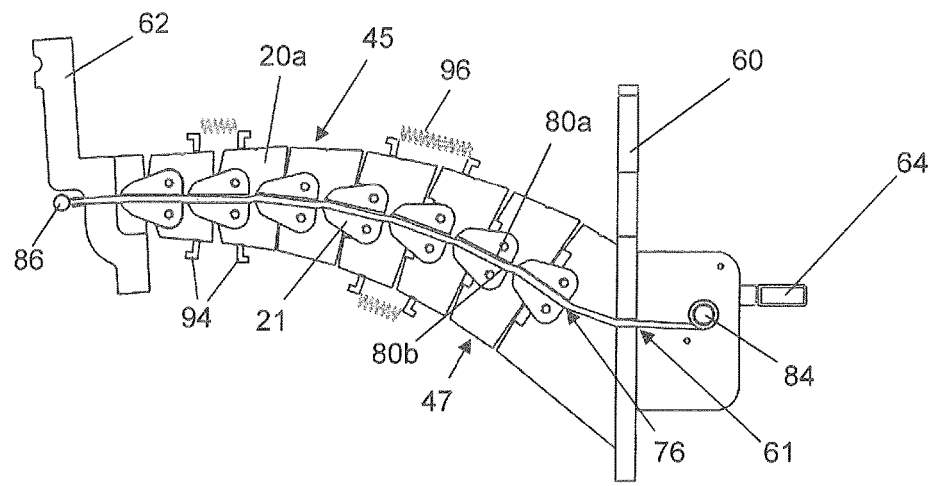

With reference now to FIG. 17C, another exemplary embodiment of the spine (13) is shown. In this embodiment, a plurality of tabs (94) are disposed on the top surfaces (45) and bottom surfaces (47) of the vertebrae (20) with a plurality of springs (96) connecting pairs of tabs (94) of adjacent vertebrae (20) to add compressive force between the vertebrae (20). As shown, springs (96) may be added to the posterior and anterior sides of the spine (13) to increase compression force between the vertebrae (20), thereby reducing the neck's range of motion without biasing the nominal position. As also shown, only a single spring (96) is attached to the tabs (94) on one side of the upper portion of the spine (13). In this configuration, the vertebrae may be biased to either extension or flexion, as desired. While only shown on the right side (20a) of the vertebrae, it should be understood that in various embodiments, tabs (94) may be provided on the left side (20b) of the vertebrae, the right side (20a) of the vertebrae, or on both the left side (20b) and the right side (20a) of the vertebrae, and any number of springs (96) may be used for added adjustability in the range of motion of the neck (13). In various embodiments, rubber bands (not shown) may be used in place of, or in addition to, springs (96) for even greater adjustability.

Figure 17D:
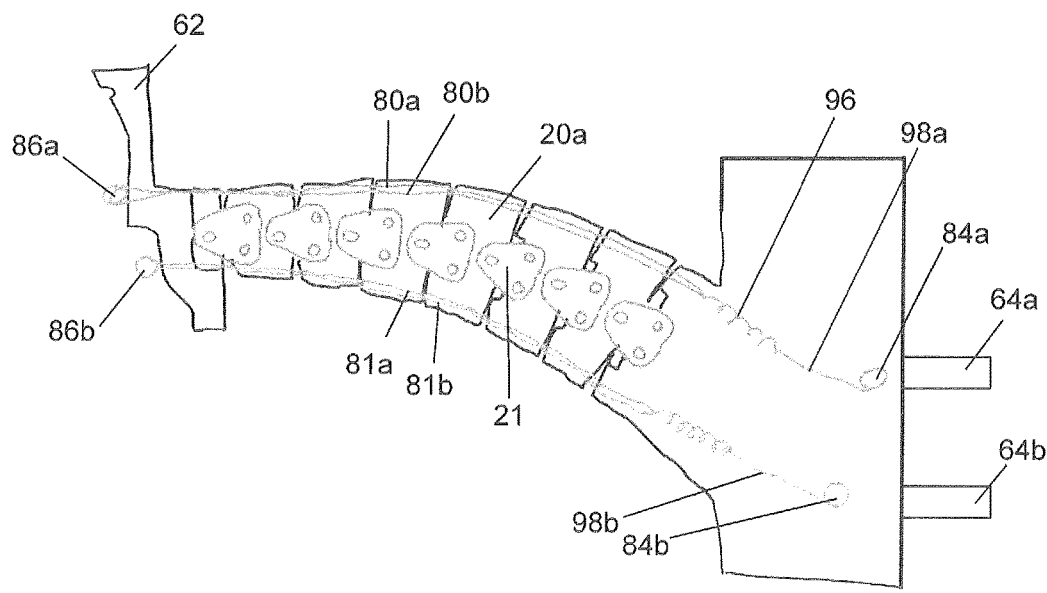

With reference now to FIG. 17D, another exemplary embodiment of the spine (13) is shown. In this embodiment, the first tensioning cable (80a, 80b) adjusts flexion on the anterior side of the neck (13), while the second tensioning cable (81a, 81b) adjusts extension on the posterior side of the neck (13). The first (80a, 80b) and second (81a, 81b) tensioning cables run through through-holes disposed in side surfaces of the individual vertebrae (20) along the respective paths shown. The first (80a, 80b) and second (81a, 81b) tensioning cables wrap around first (86a) and second (86b) pivots, each disposed at the top of the spine (13) (i.e., at the occiput which is also referred to as the C0 vertebra) at the portion of the skull (62). The ends of each of the first (80a, 80b) and second (81a, 81b) tensioning cables may then be attached to springs (96), which are in turn attached to a corresponding adjustment cable (98a, 98b). Each adjustment cable (98a, 98b) wraps around its own tightening spool (84a, 84b), each of which is rotatably connected to independent worm gearboxes (64a, 64b), as described above.

Thus, as each worm gearbox (64a, 64b) is tightened, the corresponding spring (96) stretches, thereby increasing tension in the tension cable (80a, 80b or 81a, 81b) to which it is attached. The spring (96) allows the cable to move as the spine is manipulated. If both the flexion and extension tightening cables (80, 81) are tightened simultaneously, the vertebrae (20) are brought closer together through motion in the slots on each vertebra (20) and the resulting range of motion in the neck (13) is reduced without changing the nominal position of the spine (13). However, if the flexion tightening cable (80a, 80b) is tightened more than the extension tightening cable (81a, 81b), then the neck (13) may be biased into flexion. Likewise, if the extension tightening cable (81a, 81b) is tightened more than the flexion tightening cable (80a, 80b), then the neck (13) may be biased into extension.

Stiffness of the skin, connective tissue, muscles, and ligaments of the neck, collectively described as the "neck tissue," is a factor that affects the ease with which the vocal cords can be exposed with a laryngoscope. When the tissues are stiff, greater force is required to lift them out of the way to achieve a line-of-sight view of the vocal cords. In healthy people, the neck tissues do not restrict laryngoscopy to any degree. The stiffness of the neck can increase because of various diseases and conditions. Radiation to the neck or throat to treat cancer results in fibrosis that makes the tissue extremely stiff. Other causes are extreme obesity with excessive fat causing the stiffness and various types of connective tissue disease. In severely stiff cases, it may be impossible to move that tissue out of the way, leading to failure of the procedure even though the mouth opening, the space in the mouth and throat, and the range of motion of the cervical spine are normal and would otherwise predict easy intubation.

Figure 18A:
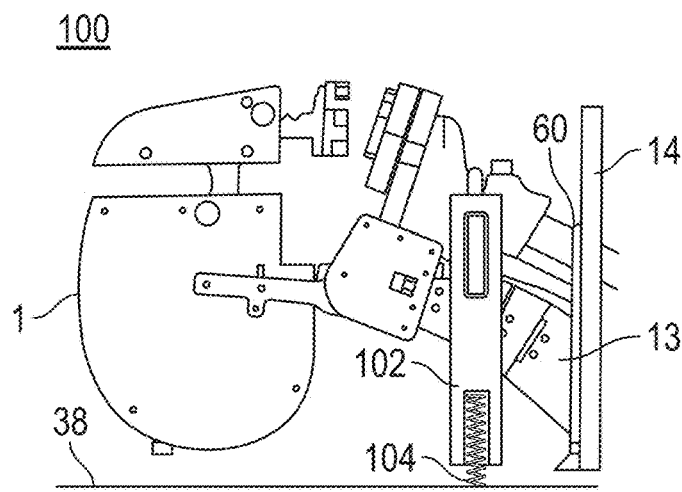
FIGS. 18A and 18B are pictorial diagrams of an exemplary embodiment of the mannequin with an elastic band applied over the supraglottic airway to mimic neck tissue stiffness.
Figure 18B:
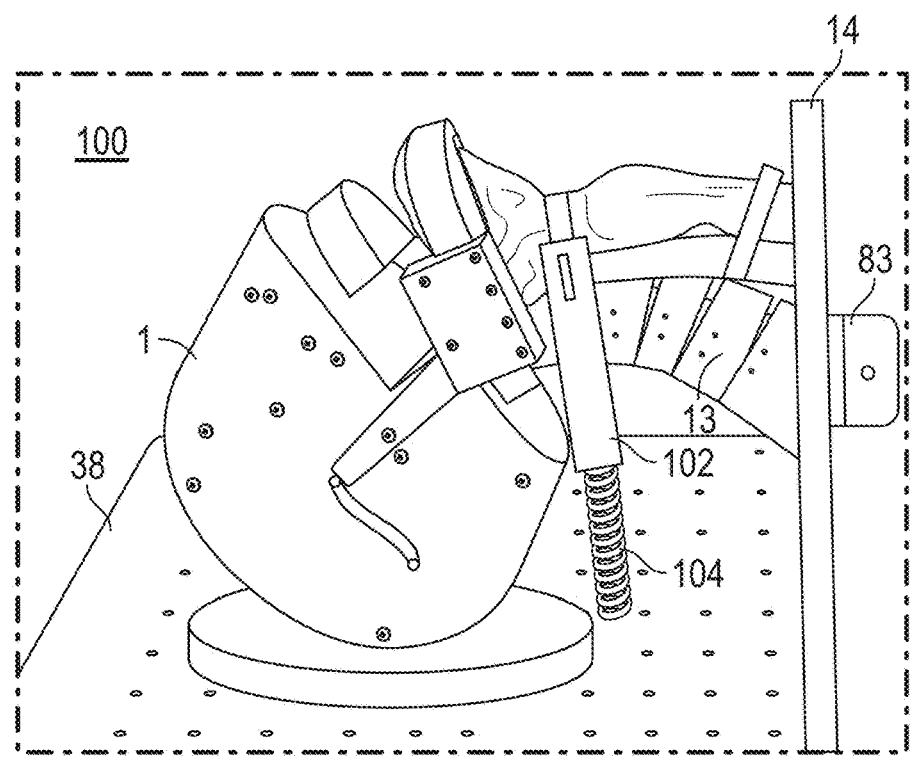

With reference now to FIGS. 18A and 18B, it may be desirable to mimic changes in neck tissue stiffness to provide a realistic environment for trainees to learn to recognize and respond to increased tissue stiffness. Such neck stiffness may be mimicked with the application of adjustable pressure on the airway just superior to the larynx. This region, rather than the tongue, is the location in the airway that causes difficulty after radiation-induced fibrosis. Thus, in certain embodiments, an elastic band (102) is applied over the supraglottic airway and attached to the baseboard (38) with one or more springs (104). The springs (104) may be locked into any one of a plurality of slots or holes disposed within the top surface of baseboard (38) and positioned at progressively greater distances from the elastic band (102). As a result of progressively greater stretch on the spring and tension on the band, greater pressure is applied to the airway just superior to the larynx, thereby mimicking tissue stiffness in the patient. The shortest distance will cause no stretch and no limitation to lift on the epiglottis.

Figure 19B:
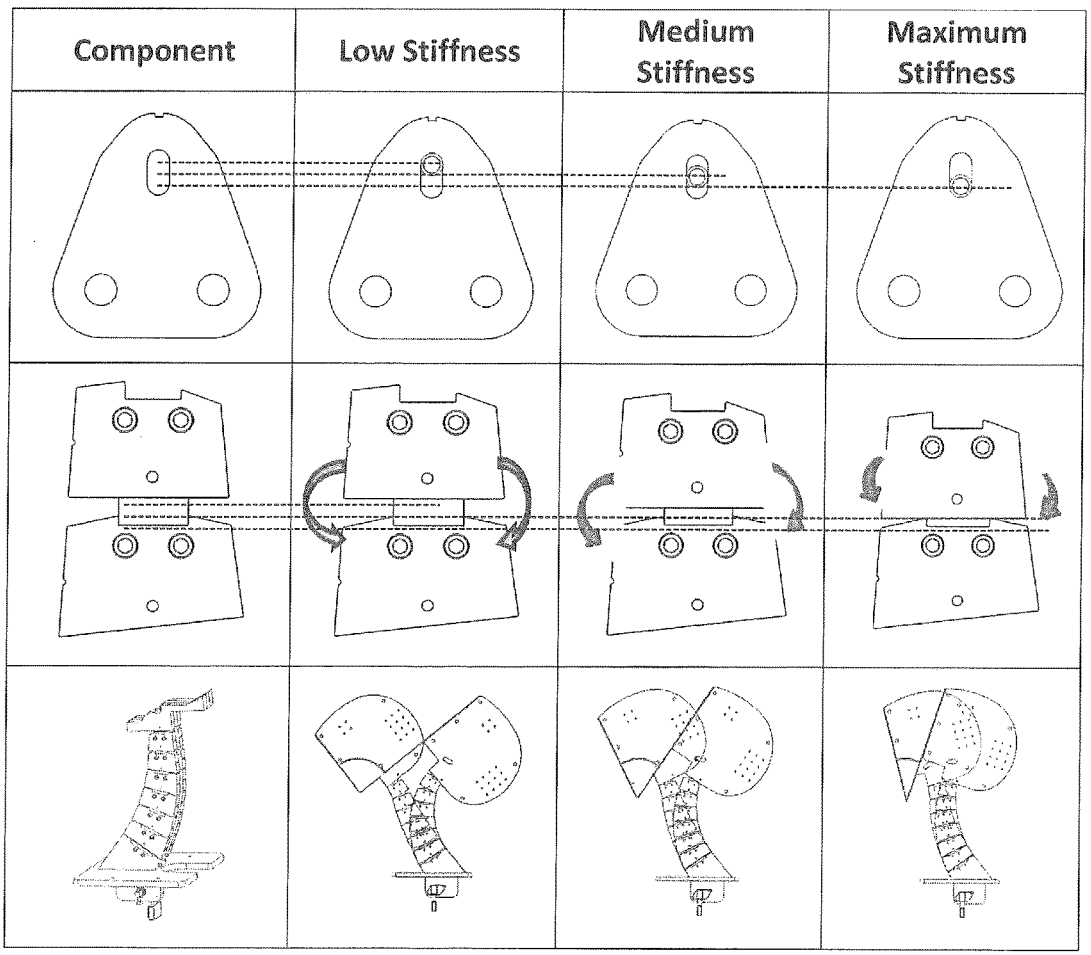

Referring now to FIG. 19B, a range of possible spine stiffnesses for the adjustable spine (13) is shown. In the low stiffness setting, the pivot pin (69) of the vertebra connector (21) is at the top of the slot (74) in the vertebrae (20) and a large range of motion between vertebrae (20) is possible (see FIG. 15A). In the medium stiffness setting, the pivot pin (69) is pulled by the cable tension towards the center of the slot (74) and less range of motion is provided. In the high stiffness setting, the cable tension is increased further and the pivot pin (69) is pulled towards the bottom of the slot (74). The vertebrae (20) are therefore squeezed even closer together and the range of motion of the spine (13) is even less.

Accordingly, the described mannequin (100) provides realistic simulation of head and neck motion for training of medical personnel. It should be understood that the various strategies for adjusting neck/spine stiffness are not mutually exclusive of each other, and therefore, it is contemplated that the mannequin (100) may include any two or more of the various adjusting strategies described above with reference to FIGS. 7, 8, 11A, 11B, 16A, 16B, 17A-17D, and 18A-18B. Thus, as described above, neck stiffness can be easily adjusted through one or more of the adjusting means including, but not limited to, varying cable tensions, spring locations and incorporation of elastic bands. This allows for a wide range of human anatomies to be used during a single training session for medical practitioners. The described design accurately models human neck motion by providing relative motion between each vertebra.

As discussed above, the adjustability provided by the mannequin (100) allows a trainee to experience anatomical variations of the human head and neck while training for airway management. During use, the maxilla may be adjusted by pulling a retaining pin outward and lifting the face upwards to lengthen/shorten the face. Similarly, the upper incisor may be adjusted by freeing the pin holding the upper teeth in place, moving the teeth forward (to shorten the inter-incisor gap) and reinserting the pin. Likewise, the mandible may be lengthened or shortened using a thumb screw on the side of the assembly. The height of the head support can be adjusted through, e.g., six different positions by pulling up on the pillow/platform (48) and rotating until the desired position is reached. Once in position, the pillow/platform (48) is shifted downward to lock back into place. Tension on the spine can be tightened or loosened with the thumb screw of the one or more worm gearboxes, thus altering the spine range of motion. With low tension, the seven-level cervical spine has a range of motion matching the range in normal human spines. Spine mobility enables the head to move up and down and to be placed in the sniff position that is desirable for laryngoscopy.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

The following examples are intended to illustrate but not limit the invention.

Example 1

Comparison of Training with Models

The subjects were medical and paramedic students receiving training in airway management, laryngoscopy, and endotracheal intubation. Medical students and paramedic students were studied on different days. Written informed consent was obtained from all subjects. A power analysis was performed before the study to estimate the necessary sample size. The assumptions were a laryngoscopy success rate during the evaluation phase of 0.9 for students with the variable anatomy training versus 0.5 for students with 1 configuration training, based on a literature report that a change in model decreased success by almost 50%. A $X^2$ test would need 24 subjects per group to detect that difference as significant at the 0.05 level with 80% probability, or 72 subjects altogether across the 3 study groups. The total number was 3 short of the target because 3 subjects who had been recruited were unable to participate. They were not replaced for reasons of convenience.

Adjustable Airway Mannequin—

The prototype for the mannequin was a 2-dimensional (2D) movable and adjustable laryngoscopy model, as described above. The model portrayed a sagittal view of the human head, neck, and spine. The dimensions, proportions, and range of motion data were extracted from human cephalometric literature and represented a realistic facsimile of the adult airway anatomy. The mechanical engineers involved with the project designed several joints and sliding parts to allow movement and adjustability. The 3D model was created by adding layers to the 2D model, extruding thickness into the transverse dimension. The 3D airway components consisted of a commercial model of the tongue, epiglottis, larynx, and trachea from Laerdal (Wappinger Falls, N.Y.). The model of the invention included a cervical spine with seven levels and physiologic range of motion, a mandible that rotates, subluxes, a tension device to close on its own, and removable upper and lower teeth. The mandible and maxilla can be lengthened or shortened independently, and mouth opening or jaw subluxation can be limited by adjusting tension elements.

Study Protocol—

Students attended a 15-minute didactic session that reviewed airway anatomy, discussed general principles of airway management, and explained the procedure for laryngoscopy. They watched a short movie illustrating laryngoscopy and observed a demonstration of the procedure on a mannequin. Subjects answered questions on a survey form about their current and previous medical occupations and prior exposure to laryngoscopy instruction.

After the didactic session, students were assigned sequentially to one of three experimental groups by order of enrollment. The "Laerdal group" practiced with the Laerdal adult intubation model. The "static group" used the new laryngoscopy training system with the mannequin maintained in the standard configuration (i.e., normal face and jaw length, normal dentition, and normal head and spine range of motion), and the "variable group" practiced on the laryngoscopy training system changing the anatomy after every five intubation attempts. In the variable group, the first configuration was standard except that the teeth were removed. Subsequent changes included replacing the teeth, lengthening the face to 0.5 cm more than normal, shortening the mandible by 0.5 cm, and finally increasing the tension on the mandible slider (i.e., movement in a prognathic direction). These variations were chosen because they target anatomic features known to affect laryngoscopy difficulty. The change in length was limited to 0.5 cm to avoid making laryngoscopy so difficult that most trainees would fail. However, the order of the configurations progressed from easiest to most difficult, with the rationale being based on data from Plummer and Owen (Plummer and Owen, Learning endotracheal intubation in a clinical skills learning center: a quantitative study, *Anesth Analg* 2001; 93:656-62) indicating that trainees learn more from a successful laryngoscopy attempt than a failed attempt. Thus, moving from easy to more difficult configurations might facilitate laryngoscopy training.

Regardless of group, each subject attempted laryngoscopy with a Macintosh no. 3 laryngoscope and endotracheal intubation with a styletted 7.0 endotracheal tube 25 times. An investigator observed and scored the result of every attempt as success or failure. A successful laryngoscopy attempt was defined as placement of the endotracheal tube into the model trachea within 30 seconds. Exceeding the time limit, intubating the model esophagus, or handling the laryngoscope in a manner that could cause oral or dental injury in a real patient were grounds for failure on the attempt.

After training on the group-specific mannequin, all students attempted direct laryngoscopy with endotracheal intubation on the adjustable model with the mouth opening reduced from 5 cm to 3.5 cm, a new configuration for all subjects. In addition, the subjects performed laryngoscopy with a different airway mannequin that none had seen, a Medical Plastics Airway® model (Mass Group, Inc., Miami, Fla.). Five attempts were recorded on each of the two evaluation models. Success or failure for each attempt was assessed as in the training period.

Laryngoscopy Force and Torque—

To obtain information on the amount of physical effort necessary for laryngoscopy on the different airway mannequins, one of the investigators with longstanding experience in laryngoscopy performed the procedure in the Laerdal, novel adjustable model, and Medical Plastics model using a Macintosh 3 blade with an instrumented laryngoscope handle. The handle incorporates a 6-axis transducer (ATI Industrial Automation, Apex, N.C.) for simultaneous measurement of force and torque. The Medical Plastics model requires significantly greater force than the other 2 mannequins, 63±3 Newton (N) vs 50±1 and 45±1 N for the adjustable and Laerdal models, respectively (P<0.001 for Medical Plastics versus either of the other 2 models). Similarly, the Medical Plastics model demonstrated the highest torque, 16±3 Newton-meters (N-m) vs 7±0.3 and 5±0.6 N-m in the same order (P<0.001 for Medical Plastics versus either of the other 2 models). For comparison, laryngoscopy in adult elective surgery patients requires approximately 44 N (range, 10-60 N) and 4 N-m (range, 2-7 N-m). Force and torque did not vary significantly for different configurations of the adjustable model (data not shown).

Data Analysis—

A mixed linear modeling approach was pursued because of the hierarchical structure of the design; multiple measurements at different occasions were nested within each subject. With a multiple measures within subjects design, mixed-level modeling can simultaneously analyze inter-individual differences (e.g., how subjects differ between one another in their trajectory across time) and intra-individual variability (i.e., how each individual manifests a unique slope and intercept/starting point). The analytic methods afford the opportunity to break down variability at multiple levels: in this case, time at the micro-level and subject at the macro-level. The method's flexibility is amplified by the ability to add time-varying predictors (level 1), time-invariant predictors (level 2), and even to analyze interactions across levels. Similar to regression analysis, one can examine each of the predictors for significance and moreover ascertain whether the slopes and/or intercepts vary randomly between subjects.

The analysis used the HLM 6.08 software, 13 testing a succession of models (i.e., unconditional model, intercepts only free to vary, slopes and intercepts free to vary, etc.). The outcome variable was laryngoscopy success or failure. Given the nonlinear (i.e., binary) nature of the outcome, a penalized quasi-likelihood approach was used for parameter estimation with the logit link function. Moreover, the estimates were reported based on the population-average results because the overarching objective was averaging over all possible values of the stochastic parameter. The logit (log of the odds), standard errors, P values, odds ratios (ORs) for success, and confidence intervals around ORs were interpreted and provided in table format.

For the linear model, the level 1 (time varying) variables were trial number, mannequin on which laryngoscopy was attempted, recent change in laryngoscopy model, and the number of previous changes in laryngoscopy model. The trial number was analyzed as either a fixed or random factor. Recent change was defined as a substitution of a new laryngoscopy mannequin or configuration for the current laryngoscopy trial or the previous trial; i.e., the variable was positive for the 2 trials after a change in mannequin. The rationale for designating the variable in this manner was our notion that a subject's performance would decrease after a change and that the subject would have to train for at least 2 laryngoscopy trials to recover the success rate obtained before the change. Level 2 (time invariant) variables included subject occupation (medical student or paramedic student), history with laryngoscopy training, and the mannequin used for training.

Differences in proportions were compared in terms of $X^2$ in a contingency table analysis. Force and torque were compared among groups by analysis of variance, and the Scheffe test was used for post hoc comparisons. The nominal level of significance was set at 0.05 for all tests.

Results—

The study population consisted of 51 paramedic students in their second month of training and 18 medical students, including 12 first-year, 3 second-year, and 3 fourth-year students. The majority of subjects had no previous exposure to laryngoscopy either in theory or practice. Eight subjects (12%) had practiced on models and three had attempted laryngoscopy on patients. Subject position and previous experience did not differ significantly among the 3 training groups.

On average, the subjects successfully intubated the model trachea in 88%±1% of the trials. Initial success rate on the first trial was on the order of 65% to 70%. From the third trial to the 25th trial, during the training run, the success rate exceeded 80% for individuals training on any of the three laryngoscopy models (i.e., the new static model, the new variable model, and the Laerdal mannequin).

The experimental design involved a time-related variable, the laryngoscopy trial number, nested within each subject. Thus, mixed linear modeling was performed to validate factors that could predict laryngoscopy success within the framework of the experiment. The significant predictors from the 2001 publication by Plummer and Owen was included in the set of variables because that study was the template for the experimental design. We first analyzed an unconditional model without predictors and found that the OR for the fixed effects was significant at 9.7. The variance component for the intercept, 0.9, was also significant, and corresponded to an intra-class correlation of 0.215. Thus, 21.5% of the variability in the results was attributable to between-individual variation and we proceeded with the hierarchical model.

In the subsequent analysis, laryngoscopy trial number, subject occupation, previous experience with laryngoscopy training, training model, laryngoscopy model, and recent change in laryngoscopy model had a significant impact on the odds of success. Based on OR, the Medical Plastics and Laerdal mannequins appeared to present the most difficulty for laryngoscopy, whereas the small mouth model and the static model seemed easiest. Success was more likely at later trial numbers and if subjects had previous experience with laryngoscopy theory or practice on mannequins. Medical students had lower odds of success than paramedic students. In addition, ORs were lower for those who trained on the static trainer (versus the Laerdal trainer), or those who experienced a recent change in laryngoscopy model (versus no change). The interaction term was calculated between training model and the recent change variable to investigate whether method of training affected the impact of change in model. The interaction term was insignificant (data not shown), suggesting that method of training did not affect the extent to which success decreased after a change.

We also evaluated training model as a factor by examining the decrease in success rates when the subjects shifted to new mannequins after the 25 attempts on their original training model. The decrease in performance was marginal when changing to the new model with limited mouth opening: 35% for subjects training on the static or variable new mannequins and a 16% decrease for subjects training with the Laerdal model. The change in success was substantially greater when subjects switched to the Medical Plastics airway dummy, consistent with the observation that laryngoscopy was more difficult with that model. Subjects training with the static model had a 90%±4% success rate for the last two trials on that model but decreased to 57%±7.4% success for the first 2 trials on the Medical Plastics model, the biggest change for any of the groups. Subjects who trained with the other two models experienced an approximately 15% decrease in performance going to the Medical Plastics model. However, the change in success did not differ among the 3 groups when analyzed by $X^2$.

While the disclosure has been described with reference to the above examples, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth. Accordingly, the invention is limited only by the following claims.

What is claimed is:

1. A training mannequin for simulation of airway management of a human being, comprising:
   (a) a skull having an upper surface and a bottom surface, wherein the skull comprises an adjustable face mounted to the upper surface of the skull, adjustable upper teeth removably attached to the adjustable face, and adjustable lower teeth removably attached to a jaw, wherein the jaw is hingedly attached to the skull;
   (b) a spine comprising a plurality of vertebrae, each connected to each other and having at least one tensioning hole disposed therein, wherein each vertebra comprises:
      (i) a pair of vertebra sides surrounding a vertebra connector;
      (ii) one or more pins rotatably attached to pivot holes disposed in opposing sides of the vertebra connector; and
      (iii) a compressible material disposed on a top surface of each vertebra side;
   (c) a first tensioning cable disposed through each tensioning hole of each vertebra;
   (d) a larynx assembly comprising a pharynx, a larynx having an upper surface and a lower surface, and a trachea, wherein the pharynx is attached to the jaw and is in contact with the spine, and the larynx is coupled to the pharynx and the trachea; and
   (e) a laryngeal position sensor fixedly mounted to the upper surface of the larynx, and an occipital position sensor mounted to the bottom surface of the skull, wherein a distal end of the spine is attached to the skull and a proximal end of the spine is configured for attachment to a spine mount.

2. The mannequin of claim 1, further comprising a spine mount attached to the proximal end of the spine.

3. The mannequin of claim 2, further comprising a first tensioning spool attached to the first tensioning cable, wherein rotation of the first tensioning spool adjusts tension in the first tensioning cable.

4. The mannequin of claim 3, further comprising a first worm gearbox disposed on a rear surface of the spine mount, and attached to the first tensioning spool, wherein the first worm gearbox is configured to rotate the first tensioning spool.

5. The mannequin of claim 2, further comprising a first pivot disposed in the skull, wherein the first tensioning cable is disposed in a double-loop format and is routed around the first pivot.

6. The mannequin of claim 2, wherein the spine has seven vertebrae, and further comprises:
   (i) a second tensioning cable disposed through the tensioning holes of each of the three vertebrae at the proximal end of the spine;
   (ii) a second pivot disposed in fourth vertebra from the proximal end of the spine, wherein the second tensioning cable is disposed in a double-loop format and is routed around the second pivot;
   (iii) a second tensioning spool attached to the second tensioning cable, wherein rotation of the second tensioning spool adjusts tension in the second tensioning cable; and
   (iv) a second worm gearbox disposed on the rear surface of the spine mount, and attached to the second tensioning spool, wherein the second worm gearbox is configured to rotate the second tensioning spool.

7. The mannequin of claim 5, further comprising:
   (i) a plurality of tabs disposed on top and bottom surfaces of each of the vertebrae; and
   (ii) a plurality of springs connecting pairs of tabs disposed on adjacent vertebrae.

8. The mannequin of claim 2, further comprising a backboard configured to accept attachment of the spine mount, wherein the trachea extends through an opening in the backboard.

9. The mannequin of claim 8, further comprising a baseboard fixedly attached to the backboard.

10. The mannequin of claim 9, further comprising an adjustable platform disposed on the baseboard and positioned in alignment with the bottom surface of the skull, wherein the platform is configured to adjust the vertical position of the skull.

11. The mannequin of claim 9, further comprising an elastic band disposed over a portion of the trachea and attached to the baseboard, wherein the elastic band is configured to apply pressure to the portion of the trachea.

12. The mannequin of claim 11, wherein the elastic band is attached to the baseboard with one or more springs.

13. The mannequin of claim 1, wherein the laryngeal position sensor and the occipital position sensor are magnetic position sensors and are configured to monitor position and rotation of the mannequin.

14. The mannequin of claim 1, further comprising one or more resistance elements attached to the jaw and the skull, wherein the elements are configured to adjust tension of the jaw.

15. The mannequin of claim 13, further comprising a data acquisition means in wireless or electrical communication with each of the sensors and configured to obtain data from one or more of the laryngeal position sensor and the occipital position sensor.

16. The mannequin of claim 15, wherein the data acquisition means is further configured to obtain data from one or more sensors mounted to a device for manipulating the airway of a human.

17. The mannequin of claim 16, wherein the device is a laryngoscope having one or more of a laryngoscope position sensor and a force sensor mounted thereto.

18. The mannequin of claim 15, wherein the data acquisition means comprises one or more of a position sensor input box and a force sensor input box.

19. The mannequin of claim 15, further comprising a display in electrical communication with the data acquisition means and configured to display real-time data to a user.

20. A training mannequin for simulation of airway management of a human being, comprising:
   (a) a skull having an upper surface and a bottom surface, wherein the skull comprises an adjustable face mounted to the upper surface of the skull, adjustable upper teeth removably attached to the adjustable face, and adjustable lower teeth removably attached to a jaw, wherein the jaw is hingedly attached to the skull;

(b) a spine comprising seven vertebrae, each vertebra being connected to each other and having at least two tensioning holes disposed therein, wherein each vertebra comprises:
  (i) a pair of vertebra sides surrounding a vertebra connector;
  (ii) one or more pins rotatably attached to pivot holes disposed in opposing sides of the vertebra connector; and
  (iii) a compressible material disposed on a top surface of each vertebra side;
(c) a first tensioning cable disposed through a first tensioning hole of each vertebra;
(d) a second tensioning cable disposed through a second tensioning hole of each vertebra;
(d) a larynx assembly comprising a pharynx, a larynx having an upper surface and a lower surface, and a trachea, wherein the pharynx is attached to the jaw and is in contact with the spine, and the larynx is coupled to the pharynx and the trachea; and
(e) a laryngeal position sensor fixedly mounted to the upper surface of the larynx, and an occipital position sensor mounted to the bottom surface of the skull,
wherein a distal end of the spine is attached to the skull and a proximal end of the spine is configured for attachment to a spine mount.

21. The mannequin of claim 20, further comprising a spine mount attached to the proximal end of the spine.

22. The mannequin of claim 21, further comprising a first tensioning spool attached to the first tensioning cable, and a second tensioning spool attached to the second tensioning cable, wherein rotation of the first tensioning spool adjusts tension in the first tensioning cable and rotation of the second tensioning spool adjusts tension in the second tensioning cable.

23. The mannequin of claim 22, further comprising a first worm gearbox disposed on a rear surface of the spine mount and attached to the first tensioning spool, and a second worm gearbox disposed on the rear surface of the spine mount and attached to the second tensioning spool, wherein the first worm gearbox is configured to rotate the first tensioning spool and the second worm gearbox is configured to rotate the second tensioning spool.

24. The mannequin of claim 21, further comprising a first pivot and a second pivot disposed in the skull, wherein the first tensioning cable is disposed in a double-loop format and is routed around the first pivot and the second tensioning cable is disposed in a double-loop format and is routed around the second pivot.

25. The mannequin of claim 24, further comprising a first spring disposed between the first tensioning cable and the first tensioning spool and a second spring disposed between the second tensioning cable and the second tensioning spool.

* * * * *